(12) United States Patent
Newcomb et al.

(10) Patent No.: US 6,653,460 B1
(45) Date of Patent: Nov. 25, 2003

(54) VOLTAGE-GATED CALCIUM CHANNEL ANTAGONIST AND METHOD

(75) Inventors: Robert Newcomb, Palo Alto, CA (US); Andrew L. Palma, San Ramon, CA (US); Balazs G. Szoke, Palo Alto, CA (US); Katalin Tarczy-Hornoch, Berkeley, CA (US); William F. Hopkins, Mountain View, CA (US); Ruth L. Cong, Fremont, CA (US); George P. Miljanich, Redwood City, CA (US); Robin Dean, Mountain View, CA (US); Laszlo Nadasdi, Walnut Creek, CA (US); Laszlo Urge, Berkeley, CA (US); Stephen Scott Bowersox, Menlo Park, CA (US)

(73) Assignee: Elan Pharmaceuticals, Inc., South San Francisco, CA (US)

( * ) Notice: Subject to any disclaimer, the term of this patent is extended or adjusted under 35 U.S.C. 154(b) by 394 days.

(21) Appl. No.: 09/640,957

(22) Filed: Aug. 16, 2000

(Under 37 CFR 1.47)

Related U.S. Application Data

(62) Division of application No. 08/904,431, filed on Aug. 1, 1997, now Pat. No. 6,156,726.
(60) Provisional application No. 60/022,978, filed on Aug. 2, 1996.

(51) Int. Cl.[7] .................. C07H 21/02; C07H 21/04; A61K 38/02; A61K 38/17

(52) U.S. Cl. .................. 536/23.1; 536/24.33; 435/6; 435/70.1; 530/300; 530/324; 530/858; 514/12; 514/21

(58) Field of Search .................. 536/23.1, 24.33; 435/6, 70.1; 514/12, 21; 530/300, 324, 858

(56) References Cited

FOREIGN PATENT DOCUMENTS

WO        WO 94/10195        5/1994

OTHER PUBLICATIONS

Ferrendelli, J.A., "Pharmacology of Antiepileptic Drugs" *Epilepsia* 28 (Suppl. 3) : S14–S16 (1987).
Jackson, H.C. and Scheideler, M.A., "Behavioural and Anticonvulsant Effects of $Ca^{2+}$ Channel Toxins in DBA/2 mice" *Psychopharmacology* 126:85–90 (1996).
Keirse, M.J.N.C., "New Perspectives for the Effective Treatment of Preterm Labor" *Am. J. Obstet. Gynecol.* 173(2) : 618–628 (1995).
Krapcho, K.J., et al., "Characterization and Cloning of Insecticidal Peptides from the Primitive Weaving Spider *Diguetia canities*" *Insect. Biochem. Mole. Biol.* 25(9) : 991–1000 (1995).
Kupferberg, H.J., "Antiepileptic Drug Development Program: A Cooperative Effort of Government and Industry" *Epilepsia* 30 (Suppl. 1) :S51–S56 (1989).
Macdonald, R.L., and Kelly, K.M., "Antiepileptie Drug Mechanisms of Action" *Epilepsia* 34 (Suppl. 5) :S1–S8 (1993).
McCombs, J., "Update on Tocolytic Therapy" *Ann. Pharmacother.* 29:515–522 (1995).
McNamara, J.O., "Development of New Pharmacological Agents for Epilepsy: Lessons from the Kindling Model" *Epilepsia.* 30(Suppl. 1):S13–S18 (1989).
Newcomb, R., et al., "SNX–325, A novel Calcium Antagonist from the Spider *Segestria florentina*" *Biochemistry* 34:8341–8347 (1995).
Piser, T., et al., "ω–Grammotoxin SIA Blocks Multiple, Voltage–Gated, $Ca^{2+}$ Channel subtypes in Cultured Rat Hippocampal Neurons" *Mol Pharmacol* 48(1) :131–139 (1995).
Wang, G., et al., "Role of Q–Type $Ca^{2+}$ Channels in Vasopressin Secretion from Neurohypophysial Terminals of the Rat" *J. Physiol. (Lond.)* 502(Pt. 2) :351–363 (1997).

*Primary Examiner*—Christopher S. F. Low
*Assistant Examiner*—Chih-Min Kam
(74) *Attorney, Agent, or Firm*—Carol A. Stratford; LeeAnn Gorthey; Perkins Coie LLP

(57) ABSTRACT

A novel class of peptides selectively block class E voltage-gated calcium channels. The class is exemplified by HG peptides such as HG-1, which is isolated from the venom-producing cells of the tarantula Hysterocrates gigas. Also disclosed are methods of producing blocking class E channels using the peptides. HG peptides have utility, for example, in inhibiting oxytocin release and for use as anticonvulsants.

5 Claims, 12 Drawing Sheets

```
HG1    GVDKAGCRYMFGGCSVNDDCCPRLGCHSLFS YCAWDLTFSD
HG2    GVDKAGCRYMFGGCTKDDDCCPRLGCKRKGYNYCAWDFTFSD
HG3    GVDKAGCRYLFGGCTRDDDCCPRLGCQLKGYNYCAWDGTFSD
R1     GVDKAGCRYMFGGCTKDDDCCPRLGCQLKGYNYCAWDFTFSD
R2     GVDKAGCRYMFGGCTKDDDCCPRLGCKLKGYNYCAWDFTFSD
R9     GVDKAGCRYMFGGCSVNDDCCPRLGCHSLFS YCAWEVTF
R11    GVDKAGCRYMFGGCSVNDDCCPRLGCHSLFS YCAWDLTF
```

Fig. 2A

```
HG1    GVDKAGCRYMFGGCSVNDDCCPRLGCHSLFS YCAWDLTFSD
HG2    GVDKAGCRYMFGGCTKDDDCCPRLGCKRKGYNYCAWDFTFSD
HG6    GVDKAGCRYMFGGCTKDDDCCPRLGCKLKGHNYCAWDFTFSD
HG7    GVDKAGCRYMFGGCTKDDDCCPRLGCKQKGNNYCAWDGTFSD
HG8    GVDKPGCRYMFGGCEKDDDCCPKLGCKDIL YYCAW   TGEF
```

Fig. 2B

```
HG1    MRTSVFVGLFVLGMICTLTSATDLKDYGKPSELISALAEVLQVDTER
HG2    MKTSVLAV FVALGLAFVLAAATEQRAN PSELVSALAEVLMLDAER
HG8    MKTSVLVV FAALALAFVLTVATEESA KPSELVSALAELVMLDAER
HG4     KTSVLAV FVALTLAFALTAATKESANTH ELVSALAELVMLDTER
```

Fig. 2C

```
HG1    GVDKAGCRYMFGGCSVNDDCCPRLGCHSLF SYCAWDLTFSD
HG2    GVDKAGCRYMFGGCTKDDDCCPRLGCKRKGYNYCAWDFTFSD
HG6    GVDKAGCRYMFGGCTKDDDCCPRLGCKLKGHNYCAWDFTFSD
HG7    GVDKAGCRYMFGGCTKDDDCCPRLGCKQKGNNYCAWDGTFSD
HG9    GVDKAGCRYLFGGCTRDDDCCPRLGCKLKGYNYCAWDGTFSD
HG8    GVDKPGCRYMFGGCEKDDDCCPKLGCKDIL YYCAW   TGEF
HG4     VDKPGCRYMFGGCTKSDDCCPKLGCKDAI  YCAWDGTV...
```

Fig. 2D

```
GVDKAGCRYMFGGCSVNDDCCPRLGC_HSLFSYCAWDLTFSD    HG1
GVDKAGCRYMFGGCTKDDDCCPRLGCKRKGYNYCAWDFTFSD    HG2
GVDKAGCRYLFGGCTRDDDCCPRLGCQLKGYNYCAWDGTFSD    HG3
             ⋀         ⊔⊔        ⊔____⊔        |
             V₁        V₂          V₃          V₄
```

Fig. 2E

```
GVDKAGCRYMFGGCSVNDDCCPRLGCHSLFS_YCAWDLTFSD    HG1
GVDKAGCRYMFGGCSVNDDCCPRLGCHSLFS_YCAWEVTF      R9
GVDKAGCRYMFGGCSVNDDCCPRLGCHSLFS_YCAWDLTF      R11
GVDKPGCRYMFGGCEKDDDCCPKLGCKDIL_YYCAW__TGEF    HG8
      CRYMFGGCSVNDDCCPRLGCHSLFS_YCAWDLTFSD    SNX-629
```

Fig. 2F

```
GVDKAGCRYMFGGCSVNDDCCPRLGCHSLFS__YCAWDLTFSD   HG1
      ECRYLFGGCKTTSDCCKHEGCKFRDK__TCAWDFTFS    Hanatoxin
      DCVRFWGKCSQTSDCCPHLACKSKWPRNICVWDGSV     S1A
```

Fig. 3

AACNGGTACGCCTGCAGGTACCGGTCCGGAATTCCCGGGTCGACCCACGCGTCCGATCAGACGAT
GCGGACTTCAGTATTTGTCGGTTTGTTTGTACTAGGGATGATTTGTACCTTAACTAGCGCCACTG
ATCTTAAAGACTATGGAAAGCCAAGTGAACTGATCAGTGCCTTAGCGGAAGTACTGCAAGTGGAC
ACTGAACGTGGAGTGGACAAAGCAGGGTGCAGGTACATGTTCGGCGGATGCAGTGTAAATGACGA
TTGCTGTCCGCGATTAGGATGCCACTCACTGTTTTCCTATTGTGCCTGGGATTTGACATTTTCCG
ATTAAATTCCAGATTCGGGTTCATTCTCAGGGATACAAACTGATAAAGAAGAATGACTCGTGCTT
TCTTTGAAATTCTGTGTTTTGATTTCAGTACATAAAAAAATACTTCCTTCTCATTTTGGCCGATT
GTGACTATTGAAATCAATAAAATTTCTGAAGCNTAAAAAAAAAAAAAAAANGGCGGCGCTT

Fig. 4A

AACNGGTACGCCTGCAGGTACCGGTCCGGAATTCCCGGGTCGACCCACGCGTCCGCATTAAACGA
TTTGTTATCGTTACTTGTCGAGATCTTGGTGACCAAATTCAGAAAGATATGAAGACCTCAGTGTT
AGCCGTCTTCGTTGCATTAGGGCTGGCTTTTGTTTTAGCTGCTGCCACTGAACAGCGTGCTAACC
CAAGCGAACTGGTCAGTGCCTTAGCGGAAGTACTGATGCTGGATGCAGAACGCGGAGTGGATAAA
GCTGGTTGTAGGTATATGTTCGGCGGATGCACAAAAGATGATGATTGTTGCCCTCGATTAGGATG
CAAACGAAAAGGATATAATTATTGCGCCTGGGATTTCACATTTAGCGACTAAACGGGAGATTTTT
GGTCAGGTCGANAACGTTATTCTCAN

Fig. 4B

AAAAAAAAAANNNNNNNNNNNNNNNNNNNNNNNNNNNAACNGGTACGCCTGCAGGTACCGGTCCGGAA
TTCCCGGGTCGACCCACGCGTCCGAGCGGATAGTTATCATTTCTTGTCGAAATCTTGATTTAGAA
ATTCAGATTCAGAAAAATATGAAGACCTCAGTTTTAGCTGTCTTTCTTGCATTAACCCTGGCTTT
TGCTTTATCTGCCGCCTCTAAGGAAAGTGCTAACACACAAGAACTAGTCAGTGCCTTAGCCGAAT
TAGTTATGTTGGATGCAGAACGTGGAGTGGACAAACCAGGCTGCAGGTATATGTTCGGCGGATGC
ACAAAGAGTGATGATTGCTGCCCGAAATTAGGATGCAAGGATGCTATTTATTGCGCTTGGGATGG
CACAGTGTNAGACTAAACCCGTGATTTTTGGTGAGATCGAAGATTTACTCCCGGAGAACCAAAT

Fig. 4C

NACCGNTACGCCTGCAGGTACCGGTCCGGAATTCCCGGGTCGACCCACGCGTCCGAGCGGATAGT
TATCATTTCTTGTCGAAATCTTGAAATTCAGATTCAGAAAAATATGAAGACCTCAGTTTTAGCTG
TCTTTGTTGCATTAACCCTGGCTTTTGCTTTAACTGCTGCCACTAAGGAAAGTGCTAACACACAT
GAACTAGTCAGTGCCTTAGCCGAATTAGTTATGTTGGATACAGAACGTGGAGTGGACAAACCAGG
CTGCAGGTATATGTTCGGCGGATGCACAAAGAGTGATGATTGCTGCCCGAAATTAGGATGCAAGG
ATGCTATTTATTGCGCTTGGGATGGCACAGTGTAAGACTAAACCCGTGATTTTTGGTGAGATCGA
AGATTCACTCTCGGAGAACCAAATNTCTTATGTTCTTC

Fig. 4D

GGGGNAAAAAAAANANNNNNNNNNNNNNNNNNNNNNNNNNNNNNCNGGTACGCCTGCAGGTACCGGTC
CGGAATTCCCGGGTCGACCCACGCGTCCGACGATTTGTTATCGTTACTTGTCGAGATCTTGGTGA
CCAAATTCAGAAAGATATGAAGACCTCAGTGTTAGCCGTCTTCGTTGCATTAGGGCTGGCTTTTG
              ↓L
TTTTAGCTGCTGCCACTGAACAGCGTGCTAACCCAAGCGAACTGGTCAGTGCCTTAGCGGAAGTA
CTGATGCTGGATGCAGAACGCGGAGTGGATAAAGCTGGTTGTAGGTATATGTTCGGCGGATGCAC
                   ├─→
AAAAGATGATGATTGTTGCCCTCGATTAGGATGCAAACTAAAAGGACATAATTATTGCGCCTGGG
ATTTCACATTTAGCGACTAAACGGGANATTTTTGGTCAGGTCNAAAACNTATTCTCAGANAAACC

Fig. 4E

CNGGTACGCCTGCAGGTACCGGTCCGGAATTCCCGGGTCGACCCACGCGTCCGAAATGATTAGCT
                                                     ↓L
ACCGTTTCTTGTCGACATCTTGGTGACCAATTCAGAAAGACATGAAGACCTCAGTGTTAGTTGTC
TTTGCTGCATTAGCGTTGGCTTTTGTTTTAACTGTTGCCACTGAAGAGAGCGCTAAACCAAGCGA
                                                  ├─→
ACTGGTCAGTGCCTTAGCGGAATTAGTGATGTTGGATGCAGAACGCGGAGTGGATAAACCAGGCT
GTAGGTATATGTTCGGCGGATGCGAAAAGATGATGATTGCTGCCCGAAATTAGGATGCAAAGAT
ATTCTTTATTATTGTGCTTGGACCGGCGAATTTTAAGACCAGACCCCAANATTTATGGTGTGGTC
GAGTATGTTATTCGGANAAAAACAAAAAAAATATCTGATGCN

Fig. 4F

AACNGGTACGCCTGCAGGTACCGGTCCGGAATTCCCGGGTCGACCCACGCGTCCGAGATCTTGGT
                      ↓L
GACCAAATTCAGAAAGATATGAAGACCTCAGTGTTAGCCGTCTTCGTTGCATTAGGGCTGGCTTT
TGTTTTAGCTGCTGCCACTGAACAGCGTGCTAACCCAAGCGAACTGGTCAGTGCCTTAGCGGAAG
                                              ├─→
TTCTGATGCTGGATGCAGAACGCGGAGTGGATAAAGCAGGCTGCAGGTATCTATTCGGCGGATGC
ACAAGAGATGATGATTGCTGCCCTCGATTGGGATGCAAACTAAAAGGATATAATTATTGCGCCTG
GGATGGAACATTTAGCGACTAAACCGGAGTTTTTGGCGAAGTCGAGAACGTNTTCTCAGANAAAG
CAAAGAATATTTGATGTTTTCCTTTGATGATTTAAC

Fig. 4G

SEQUENCE LISTING

<160> NUMBER OF SEQ ID NOS: 56

<210> SEQ ID NO 1
<211> LENGTH: 41
<212> TYPE: PRT
<213> ORGANISM: Hysterocrates gigas

<400> SEQUENCE: 1

Gly Val Asp Lys Ala Gly Cys Arg Tyr Met Phe Gly Gly Cys Ser Val
1               5                   10                  15

Asn Asp Asp Cys Cys Pro Arg Leu Gly Cys His Ser Leu Phe Ser Tyr
            20                  25                  30

Cys Ala Trp Asp Leu Thr Phe Ser Asp
        35                  40

<210> SEQ ID NO 2
<211> LENGTH: 42
<212> TYPE: PRT
<213> ORGANISM: Hysterocrates gigas

<400> SEQUENCE: 2

Gly Val Asp Lys Ala Gly Cys Arg Tyr Met Phe Gly Gly Cys Thr Lys
1               5                   10                  15

```
Asp Asp Asp Cys Cys Pro Arg Leu Gly Cys Lys Arg Lys Gly Tyr Asn
            20                  25                  30

Tyr Cys Ala Trp Asp Phe Thr Phe Ser Asp
            35                  40

<210> SEQ ID NO 3
<211> LENGTH: 42
<212> TYPE: PRT
<213> ORGANISM: Hysterocrates gigas

<400> SEQUENCE: 3

Gly Val Asp Lys Ala Gly Cys Arg Tyr Leu Phe Gly Gly Cys Thr Arg
 1               5                  10                  15

Asp Asp Asp Cys Cys Pro Arg Leu Gly Cys Gln Leu Lys Gly Tyr Asn
            20                  25                  30

Tyr Cys Ala Trp Asp Gly Thr Phe Ser Asp
            35                  40

<210> SEQ ID NO 4
<211> LENGTH: 37
<212> TYPE: PRT
<213> ORGANISM: Hysterocrates gigas

<400> SEQUENCE: 4

Val Asp Lys Pro Gly Cys Arg Tyr Met Phe Gly Gly Cys Thr Lys Ser
 1               5                  10                  15

Asp Asp Cys Cys Pro Lys Leu Gly Cys Lys Asp Ala Ile Tyr Cys Ala
            20                  25                  30

Trp Asp Gly Thr Val
            35

<210> SEQ ID NO 5
<211> LENGTH: 7
<212> TYPE: PRT
<213> ORGANISM: Hysterocrates gigas

<400> SEQUENCE: 5

Gly Val Asp Lys Ala Gly Cys
 1               5

<210> SEQ ID NO 6
<211> LENGTH: 42
<212> TYPE: PRT
<213> ORGANISM: Hysterocrates gigas

<400> SEQUENCE: 6

Gly Val Asp Lys Ala Gly Cys Arg Tyr Met Phe Gly Gly Cys Thr Lys
 1               5                  10                  15

Asp Asp Asp Cys Cys Pro Arg Leu Gly Cys Lys Leu Lys Gly His Asn
            20                  25                  30

Tyr Cys Ala Trp Asp Phe Thr Phe Ser Asp
            35                  40

<210> SEQ ID NO 7
<211> LENGTH: 42
<212> TYPE: PRT
<213> ORGANISM: Hysterocrates gigas

<400> SEQUENCE: 7

Gly Val Asp Lys Ala Gly Cys Arg Tyr Met Phe Gly Gly Cys Thr Lys
 1               5                  10                  15
```

Asp Asp Asp Cys Cys Pro Arg Leu Gly Cys Lys Gln Lys Gly Asn Asn
            20                  25                  30

Tyr Cys Ala Trp Asp Gly Thr Phe Ser Asp
        35                  40

<210> SEQ ID NO 8
<211> LENGTH: 39
<212> TYPE: PRT
<213> ORGANISM: Hysterocrates gigas

<400> SEQUENCE: 8

Gly Val Asp Lys Pro Gly Cys Arg Tyr Met Phe Gly Gly Cys Glu Lys
1               5                   10                  15

Asp Asp Asp Cys Cys Pro Lys Leu Gly Cys Lys Asp Ile Leu Tyr Tyr
            20                  25                  30

Cys Ala Trp Thr Gly Glu Phe
        35

<210> SEQ ID NO 9
<211> LENGTH: 42
<212> TYPE: PRT
<213> ORGANISM: Hysterocrates gigas

<400> SEQUENCE: 9

Gly Val Asp Lys Ala Gly Cys Arg Tyr Leu Phe Gly Gly Cys Thr Arg
1               5                   10                  15

Asp Asp Asp Cys Cys Pro Arg Leu Gly Cys Lys Leu Lys Gly Tyr Asn
            20                  25                  30

Tyr Cys Ala Trp Asp Gly Thr Phe Ser Asp
        35                  40

<210> SEQ ID NO 10
<211> LENGTH: 4
<212> TYPE: PRT
<213> ORGANISM: Hysterocrates gigas

<400> SEQUENCE: 10

Tyr Cys Ala Trp
1

<210> SEQ ID NO 11
<211> LENGTH: 42
<212> TYPE: PRT
<213> ORGANISM: Hysterocrates gigas

<400> SEQUENCE: 11

Gly Val Asp Lys Ala Gly Cys Arg Tyr Met Phe Gly Gly Cys Thr Lys
1               5                   10                  15

Asp Asp Asp Cys Cys Pro Arg Leu Gly Cys Gln Leu Lys Gly Tyr Asn
            20                  25                  30

Tyr Cys Ala Trp Asp Phe Thr Phe Ser Asp
        35                  40

<210> SEQ ID NO 12
<211> LENGTH: 42
<212> TYPE: PRT
<213> ORGANISM: Hysterocrates gigas

<400> SEQUENCE: 12

Gly Val Asp Lys Ala Gly Cys Arg Tyr Met Phe Gly Gly Cys Thr Lys
1               5                   10                  15

Asp Asp Asp Cys Cys Pro Arg Leu Gly Cys Lys Leu Lys Gly Tyr Asn
            20                  25                  30

Tyr Cys Ala Trp Asp Phe Thr Phe Ser Asp
        35                  40

<210> SEQ ID NO 13
<211> LENGTH: 39
<212> TYPE: PRT
<213> ORGANISM: Hysterocrates gigas

<400> SEQUENCE: 13

Gly Val Asp Lys Ala Gly Cys Arg Tyr Met Phe Gly Gly Cys Ser Val
 1               5                  10                  15

Asn Asp Asp Cys Cys Pro Arg Leu Gly Cys His Ser Leu Phe Ser Tyr
            20                  25                  30

Cys Ala Trp Glu Val Thr Phe
        35

<210> SEQ ID NO 14
<211> LENGTH: 39
<212> TYPE: PRT
<213> ORGANISM: Hysterocrates gigas

<400> SEQUENCE: 14

Gly Val Asp Lys Ala Gly Cys Arg Tyr Met Phe Gly Gly Cys Ser Val
 1               5                  10                  15

Asn Asp Asp Cys Cys Pro Arg Leu Gly Cys His Ser Leu Phe Ser Tyr
            20                  25                  30

Cys Ala Trp Asp Leu Thr Phe
        35

<210> SEQ ID NO 15
<211> LENGTH: 35
<212> TYPE: PRT
<213> ORGANISM: Artificial Sequence
<220> FEATURE:
<223> OTHER INFORMATION: synthetic

<400> SEQUENCE: 15

Cys Arg Tyr Met Phe Gly Gly Cys Ser Val Asn Asp Asp Cys Cys Pro
 1               5                  10                  15

Arg Leu Gly Cys His Ser Leu Phe Ser Tyr Cys Ala Trp Asp Leu Thr
            20                  25                  30

Phe Ser Asp
        35

<210> SEQ ID NO 16
<211> LENGTH: 9
<212> TYPE: PRT
<213> ORGANISM: Hysterocrates gigas

<400> SEQUENCE: 16

Gly Val Asp Lys Ala Gly Cys Arg Tyr
 1               5

<210> SEQ ID NO 17
<211> LENGTH: 9
<212> TYPE: PRT
<213> ORGANISM: Hysterocrates gigas

<400> SEQUENCE: 17

Asp Asp Cys Cys Pro Arg Leu Gly Cys

```
<210> SEQ ID NO 18
<211> LENGTH: 5
<212> TYPE: PRT
<213> ORGANISM: Hysterocrates gigas

<400> SEQUENCE: 18

Tyr Cys Ala Trp Asp
 1               5

<210> SEQ ID NO 19
<211> LENGTH: 8
<212> TYPE: PRT
<213> ORGANISM: Hysterocrates gigas

<400> SEQUENCE: 19

Cys Arg Tyr Met Phe Gly Gly Cys
 1               5

<210> SEQ ID NO 20
<211> LENGTH: 5
<212> TYPE: PRT
<213> ORGANISM: Hysterocrates gigas

<400> SEQUENCE: 20

Asp Asp Cys Cys Pro
 1               5

<210> SEQ ID NO 21
<211> LENGTH: 45
<212> TYPE: PRT
<213> ORGANISM: Hysterocrates gigas

<400> SEQUENCE: 21

Met Lys Thr Ser Val Leu Val Val Phe Ala Ala Leu Ala Leu Ala Phe
 1               5                  10                  15

Val Leu Thr Val Ala Thr Glu Glu Ser Ala Lys Pro Ser Glu Leu Val
                20                  25                  30

Ser Ala Leu Ala Glu Leu Val Met Leu Asp Ala Glu Arg
            35                  40                  45

<210> SEQ ID NO 22
<211> LENGTH: 44
<212> TYPE: PRT
<213> ORGANISM: Hysterocrates gigas

<400> SEQUENCE: 22

Lys Thr Ser Val Leu Ala Val Phe Val Ala Leu Thr Leu Ala Phe Ala
 1               5                  10                  15

Leu Thr Ala Ala Thr Lys Glu Ser Ala Asn Thr His Glu Leu Val Ser
                20                  25                  30

Ala Leu Ala Glu Leu Val Met Leu Asp Thr Glu Arg
            35                  40

<210> SEQ ID NO 23
<211> LENGTH: 141
<212> TYPE: DNA
<213> ORGANISM: Hysterocrates gigas

<400> SEQUENCE: 23
atgcggactt cagtatttgt cggtttgttt gtactaggga tgatttgtac cttaactagc      60
```

```
gccactgatc ttaaagacta tggaaagcca agtgaactga tcagtgcctt agcggaagta    120
ctgcaagtgg acactgaacg t                                              141
```

<210> SEQ ID NO 24
<211> LENGTH: 123
<212> TYPE: DNA
<213> ORGANISM: Hysterocrates gigas

<400> SEQUENCE: 24

```
ggagtggaca aagcagggtg caggtacatg ttcggcggat gcagtgtaaa tgacgattgc    60
tgtccgcgat taggatgcca ctcactgttt tcctattgtg cctgggattt gacattttcc   120
gat                                                                 123
```

<210> SEQ ID NO 25
<211> LENGTH: 516
<212> TYPE: DNA
<213> ORGANISM: Hysterocrates gigas
<220> FEATURE:
<221> NAME/KEY: misc_feature
<222> LOCATION: 4, 488, 506
<223> OTHER INFORMATION: n = A,T/U,C or G

<400> SEQUENCE: 25

```
aacnggtacg cctgcaggta ccggtccgga attcccgggt cgacccacgc gtccgatcag    60
acgatgcgga cttcagtatt tgtcggtttg tttgtactag ggatgatttg taccttaact   120
agcgccactg atcttaaaga ctatggaaag ccaagtgaac tgatcagtgc cttagcggaa   180
gtactgcaag tggacactga acgtggagtg gacaaagcag ggtgcaggta catgttcggc   240
ggatgcagtg taaatgacga ttgctgtccg cgattaggat gccactcact gttttcctat   300
tgtgcctggg atttgacatt ttccgattaa attccagatt cgggttcatt ctcagggata   360
caaactgata agaagaatg actcgtgctt tctttgaaat tctgtgtttt gatttcagta    420
cataaaaaaa tacttccttc tcattttggc cgattgtgac tattgaaatc aataaaattt   480
ctgaagcnta aaaaaaaaaa aaaaanggcg gcgctt                             516
```

<210> SEQ ID NO 26
<211> LENGTH: 198
<212> TYPE: DNA
<213> ORGANISM: Hysterocrates gigas

<400> SEQUENCE: 26

```
gtccgcatta aacgatttgt tatcgttact tgtcgagatc ttggtgacca aattcagaaa    60
gatatgaaga cctcagtgtt agccgtcttc gttgcattag ggctggcttt tgttttagct   120
gctgccactg aacagcgtgc taacccaagc gaactggtca gtgccttagc ggaagtactg   180
atgctggatg cagaacgc                                                 198
```

<210> SEQ ID NO 27
<211> LENGTH: 126
<212> TYPE: DNA
<213> ORGANISM: Hysterocrates gigas

<400> SEQUENCE: 27

```
ggagtggata aagctggttg taggtatatg ttcggcggat gcacaaaaga tgatgattgt    60
tgccctcgat taggatgcaa acgaaaagga tataattatt gcgcctggga tttcacattt   120
agcgac                                                              126
```

```
<210> SEQ ID NO 28
<211> LENGTH: 416
<212> TYPE: DNA
<213> ORGANISM: Hysterocrates gigas
<220> FEATURE:
<221> NAME/KEY: misc_feature
<222> LOCATION: 4, 402, 416
<223> OTHER INFORMATION: n = A,T/U,C or G

<400> SEQUENCE: 28
aacnggtacg cctgcaggta ccggtccgga attcccgggt cgacccacgc gtccgcatta      60
aacgatttgt tatcgttact tgtcgagatc ttggtgacca aattcagaaa gatatgaaga     120
cctcagtgtt agccgtcttc gttgcattag ggctggcttt tgttttagct gctgccactg     180
aacagcgtgc taacccaagc gaactggtca gtgccttagc ggaagtactg atgctggatg     240
cagaacgcgg agtggataaa gctggttgta ggtatatgtt cggcggatgc acaaaagatg     300
atgattgttg ccctcgatta ggatgcaaac gaaaaggata taattattgc gcctgggatt     360
tcacatttag cgactaaacg ggagattttt ggtcaggtcg anaacgttat tctcan        416

<210> SEQ ID NO 29
<211> LENGTH: 135
<212> TYPE: DNA
<213> ORGANISM: Hysterocrates gigas

<400> SEQUENCE: 29
atgaagacct cagttttagc tgtctttctt gcattaaccc tggcttttgc tttatctgcc     60
gcctctaagg aaagtgctaa cacacaagaa ctagtcagtg ccttagccga attagttatg    120
ttggatgcag aacgt                                                      135

<210> SEQ ID NO 30
<211> LENGTH: 114
<212> TYPE: DNA
<213> ORGANISM: Hysterocrates gigas

<400> SEQUENCE: 30
ggagtggaca aaccaggctg caggtatatg ttcggcggat gcacaaagag tgatgattgc     60
tgcccgaaat taggatgcaa ggatgctatt tattgcgctt gggatggcac agtg          114

<210> SEQ ID NO 31
<211> LENGTH: 454
<212> TYPE: DNA
<213> ORGANISM: Hysterocrates gigas
<220> FEATURE:
<221> NAME/KEY: misc_feature
<222> LOCATION: 10-34, 38, 399
<223> OTHER INFORMATION: n = A,T/U,C or G

<400> SEQUENCE: 31
aaaaaaaaan nnnnnnnnnn nnnnnnnnnn nnnnaacngg tacgcctgca ggtaccggtc     60
cggaattccc gggtcgaccc acgcgtccga gcggatagtt atcatttctt gtcgaaatct    120
tgatttagaa attcagattc agaaaaatat gaagacctca gttttagctg tctttcttgc    180
attaaccctg gcttttgctt tatctgccgc ctctaaggaa agtgctaaca cacaagaact    240
agtcagtgcc ttagccgaat tagttatgtt ggatgcagaa cgtggagtgg acaaaccagg    300
ctgcaggtat atgttcggcg gatgcacaaa gagtgatgat tgctgcccga aattaggatg    360
caaggatgct atttattgcg cttgggatgg cacagtgtna gactaaaccc gtgattttg    420 gtgagatcga agatttactc ccggagaacc aaat                                 454
```

<210> SEQ ID NO 32
<211> LENGTH: 135
<212> TYPE: DNA
<213> ORGANISM: Hysterocrates gigas

<400> SEQUENCE: 32

| | | |
|---|---|---|
| atgaagacct cagttttagc tgtctttgtt gcattaaccc tggcttttgc tttaactgct | | 60 |
| gccactaagg aaagtgctaa cacacatgaa ctagtcagtg ccttagccga attagttatg | | 120 |
| ttggatacag aacgt | | 135 |

<210> SEQ ID NO 33
<211> LENGTH: 114
<212> TYPE: DNA
<213> ORGANISM: Hysterocrates gigas

<400> SEQUENCE: 33

| | | |
|---|---|---|
| ggagtggaca aaccaggctg caggtatatg ttcggcggat gcacaaagag tgatgattgc | | 60 |
| tgcccgaaat taggatgcaa ggatgctatt tattgcgctt gggatggcac agtg | | 114 |

<210> SEQ ID NO 34
<211> LENGTH: 428
<212> TYPE: DNA
<213> ORGANISM: Hysterocrates gigas
<220> FEATURE:
<221> NAME/KEY: misc_feature
<222> LOCATION: 1, 6, 415
<223> OTHER INFORMATION: n = A,T/U,C or G

<400> SEQUENCE: 34

| | | |
|---|---|---|
| naccgntacg cctgcaggta ccggtccgga attcccgggt cgacccacgc gtccgagcgg | | 60 |
| atagttatca tttcttgtcg aaatcttgaa attcagattc agaaaaatat gaagacctca | | 120 |
| gttttagctg tctttgttgc attaaccctg gcttttgctt taactgctgc cactaaggaa | | 180 |
| agtgctaaca cacatgaact agtcagtgcc ttagccgaat tagttatgtt ggatacagaa | | 240 |
| cgtggagtgg acaaaccagg ctgcaggtat atgttcggcg gatgcacaaa gagtgatgat | | 300 |
| tgctgcccga aattaggatg caaggatgct atttattgcg cttgggatgg cacagtgtaa | | 360 |
| gactaaaccc gtgattttg gtgagatcga agattcactc tcggagaacc aaatntctta | | 420 |
| tgttcttc | | 428 |

<210> SEQ ID NO 35
<211> LENGTH: 135
<212> TYPE: DNA
<213> ORGANISM: Hysterocrates gigas

<400> SEQUENCE: 35

| | | |
|---|---|---|
| atgaagacct cagtgttagc cgtcttcgtt gcattagggc tggcttttgt tttagctgct | | 60 |
| gccactgaac agcgtgctaa cccaagcgaa ctggtcagtg ccttagcgga agtactgatg | | 120 |
| ctggatgcag aacgc | | 135 |

<210> SEQ ID NO 36
<211> LENGTH: 174
<212> TYPE: DNA
<213> ORGANISM: Hysterocrates gigas
<220> FEATURE:
<221> NAME/KEY: misc_feature
<222> LOCATION: 136, 152, 158, 169
<223> OTHER INFORMATION: n = A,T/U,C or G

<400> SEQUENCE: 36

```
ggagtggata aagctggttg taggtatatg ttcggcggat gcacaaaaga tgatgattgt      60
tgccctcgat taggatgcaa actaaaagga cataattatt gcgcctggga tttcacattt     120
agcgactaaa cgggananttt ttggtcaggt cnaaaacnta ttctcagana aacc          174

<210> SEQ ID NO 37
<211> LENGTH: 455
<212> TYPE: DNA
<213> ORGANISM: Hysterocrates gigas
<220> FEATURE:
<221> NAME/KEY: misc_feature
<222> LOCATION: 5, 14, 16-41, 43, 417, 433, 439, 450
<223> OTHER INFORMATION: n = A,T/U,C or G

<400> SEQUENCE: 37
ggggnaaaaa aaanannnnn nnnnnnnnnn nnnnnnnnnn ncnggtacgc ctgcaggtac      60
cggtccggaa ttcccgggtc gacccacgcg tccgacgatt tgttatcgtt acttgtcgag    120
atcttggtga ccaaattcag aaagatatga agacctcagt gttagccgtc ttcgttgcat    180
tagggctggc ttttgtttta gctgctgcca ctgaacagcg tgctaaccca agcgaactgg    240
tcagtgcctt agcggaagta ctgatgctgg atgcagaacg cggagtggat aaagctggtt    300
gtaggtatat gttcggcgga tgcacaaaag atgatgattg ttgccctcga ttaggatgca    360
aactaaaagg acataattat tgcgcctggg atttcacatt tagcgactaa acgggganatt    420 tttggtcagg tcnaaaacnt attctcagan aaacc                              455

<210> SEQ ID NO 38
<211> LENGTH: 135
<212> TYPE: DNA
<213> ORGANISM: Hysterocrates gigas

<400> SEQUENCE: 38
atgaagacct cagtgttagt tgtctttgct gcattagcgt tggcttttgt tttaactgtt     60
gccactgaag agagcgctaa accaagcgaa ctggtcagtg ccttagcgga attagtgatg    120
ttggatgcag aacgc                                                    135

<210> SEQ ID NO 39
<211> LENGTH: 191
<212> TYPE: DNA
<213> ORGANISM: Hysterocrates gigas
<220> FEATURE:
<221> NAME/KEY: misc_feature
<222> LOCATION: 134, 166, 191
<223> OTHER INFORMATION: n = A,T/U,C or G

<400> SEQUENCE: 39
ggagtggata aaccaggctg taggtatatg ttcggcggat gcgaaaaaga tgatgattgc      60
tgcccgaaat taggatgcaa agatattctt tattattgtg cttggaccgg cgaattttaa    120
gaccagaccc caanatttat ggtgtggtcg agtatgttat tcgganaaaa acaaaaaaaa    180
tatctgatgc n                                                        191

<210> SEQ ID NO 40
<211> LENGTH: 432
<212> TYPE: DNA
<213> ORGANISM: Hysterocrates gigas
<220> FEATURE:
<221> NAME/KEY: misc_feature
<222> LOCATION: 2, 375, 407, 432
<223> OTHER INFORMATION: n = A,T/U,C or G
```

-continued

```
<400> SEQUENCE: 40
cnggtacgcc tgcaggtacc ggtccggaat tcccgggtcg acccacgcgt ccgaaatgat       60
tagctaccgt ttcttgtcga catcttggtg accaattcag aaagacatga agacctcagt      120
gttagttgtc tttgctgcat tagcgttggc ttttgtttta actgttgcca ctgaagagag      180
cgctaaacca agcgaactgg tcagtgcctt agcggaatta gtgatgttgg atgcagaacg      240
cggagtggat aaaccaggct gtaggtatat gttcggcgga tgcgaaaaag atgatgattg      300
ctgcccgaaa ttaggatgca agatattct ttattattgt gcttggaccg gcgaatttta       360
agaccagacc ccaanattta tggtgtggtc gagtatgtta ttcgganaaa aacaaaaaaa      420
atatctgatg cn                                                          432

<210> SEQ ID NO 41
<211> LENGTH: 135
<212> TYPE: DNA
<213> ORGANISM: Hysterocrates gigas

<400> SEQUENCE: 41
atgaagacct cagtgttagc cgtcttcgtt gcattagggc tggcttttgt tttagctgct       60
gccactgaac agcgtgctaa cccaagcgaa ctggtcagtg ccttagcgga agttctgatg      120
ctggatgcag aacgc                                                       135

<210> SEQ ID NO 42
<211> LENGTH: 208
<212> TYPE: DNA
<213> ORGANISM: Hysterocrates gigas
<220> FEATURE:
<221> NAME/KEY: misc_feature
<222> LOCATION: 159, 168
<223> OTHER INFORMATION: n = A,T/U,C or G

<400> SEQUENCE: 42
ggagtggata aagcaggctg caggtatcta ttcggcggat gcacaagaga tgatgattgc       60
tgccctcgat tgggatgcaa actaaaagga tataattatt gcgcctggga tggaacatttt     120 agcgactaaa ccggagtttt tggcgaagtc gagaacgtnt tctcaganaa agcaaagaat      180
atttgatgtt tcctttgat gatttaac                                          208

<210> SEQ ID NO 43
<211> LENGTH: 426
<212> TYPE: DNA
<213> ORGANISM: Hysterocrates gigas
<220> FEATURE:
<221> NAME/KEY: misc_feature
<222> LOCATION: 4, 377, 386
<223> OTHER INFORMATION: n = A,T/U,C or G

<400> SEQUENCE: 43
aacnggtacg cctgcaggta ccggtccgga attcccgggt cgacccacgc gtccgagatc       60
ttggtgacca aattcagaaa gatatgaaga cctcagtgtt agccgtcttc gttgcattag      120
ggctggcttt tgttttagct gctgccactg aacagcgtgc taacccaagc gaactggtca      180
gtgccttagc ggaagttctg atgctggatg cagaacgcgg agtggataaa gcaggctgca      240
ggtatctatt cggcggatgc acaagagatg atgattgctg ccctcgattg ggatgcaaac      300
taaaaggata taattattgc gcctgggatg gaacatttag cgactaaacc ggagtttttg      360
gcgaagtcga gaacgtnttc tcaganaaag caaagaatat ttgatgtttt cctttgatga      420
tttaac                                                                 426
```

<210> SEQ ID NO 44
<211> LENGTH: 35
<212> TYPE: PRT
<213> ORGANISM: Grammostola spatulata

<400> SEQUENCE: 44

Glu Cys Arg Tyr Leu Phe Gly Gly Cys Lys Thr Thr Ser Asp Cys Cys
1               5                   10                  15

Lys His Glu Gly Cys Lys Phe Arg Asp Lys Thr Cys Ala Trp Asp Phe
            20                  25                  30

Thr Phe Ser
        35

<210> SEQ ID NO 45
<211> LENGTH: 36
<212> TYPE: PRT
<213> ORGANISM: Grammostola spatulata
<220> FEATURE:
<221> NAME/KEY: VARIANT
<222> LOCATION: 19
<223> OTHER INFORMATION: Xaa = Any Amino Acid

<400> SEQUENCE: 45

Asp Cys Val Arg Phe Trp Gly Lys Cys Ser Gln Thr Ser Asp Cys Cys
1               5                   10                  15

Pro His Xaa Ala Cys Lys Ser Lys Trp Pro Arg Asn Ile Cys Val Trp
            20                  25                  30

Asp Gly Ser Val
        35

<210> SEQ ID NO 46
<211> LENGTH: 33
<212> TYPE: DNA
<213> ORGANISM: Artificial Sequence
<220> FEATURE:
<223> OTHER INFORMATION: GSP1 (degenerate oligonucleotide primer)

<400> SEQUENCE: 46
caucaucauc auggygtsga yaaggctggy tgc                              33

<210> SEQ ID NO 47
<211> LENGTH: 30
<212> TYPE: DNA
<213> ORGANISM: Artificial Sequence
<220> FEATURE:
<223> OTHER INFORMATION: GSP2 (degenerate oligonucleotide primer)

<400> SEQUENCE: 47
cuacuacuac uagaargtsa rrtcccargc                                  30

<210> SEQ ID NO 48
<211> LENGTH: 47
<212> TYPE: PRT
<213> ORGANISM: Hysterocrates gigas

<400> SEQUENCE: 48

Met Arg Thr Ser Val Phe Val Gly Leu Phe Val Leu Gly Met Ile Cys
1               5                   10                  15

Thr Leu Thr Ser Ala Thr Asp Leu Lys Asp Tyr Gly Lys Pro Ser Glu
            20                  25                  30

Leu Ile Ser Ala Leu Ala Glu Val Leu Gln Val Asp Thr Glu Arg
        35                  40                  45

<210> SEQ ID NO 49
<211> LENGTH: 45
<212> TYPE: PRT
<213> ORGANISM: Hysterocrates gigas

<400> SEQUENCE: 49

Met Lys Thr Ser Val Leu Ala Val Phe Val Ala Leu Gly Leu Ala Phe
 1               5                  10                  15

Val Leu Ala Ala Ala Thr Glu Gln Arg Ala Asn Pro Ser Glu Leu Val
                20                  25                  30

Ser Ala Leu Ala Glu Val Leu Met Leu Asp Ala Glu Arg
            35                  40                  45

<210> SEQ ID NO 50
<211> LENGTH: 21
<212> TYPE: DNA
<213> ORGANISM: Artificial Sequence
<220> FEATURE:
<223> OTHER INFORMATION: HG-1 primer
<220> FEATURE:
<221> NAME/KEY: misc_feature
<222> LOCATION: 3, 9, 15, 18
<223> OTHER INFORMATION: n = C or T
<220> FEATURE:
<221> NAME/KEY: misc_feature
<222> LOCATION: 6
<223> OTHER INFORMATION: n = C or G

<400> SEQUENCE: 50
ggngtngana aggcnggntg c                                          21

<210> SEQ ID NO 51
<211> LENGTH: 6
<212> TYPE: PRT
<213> ORGANISM: Hysterocrates gigas
<220> FEATURE:
<221> NAME/KEY: VARIANT
<222> LOCATION: 5
<223> OTHER INFORMATION: Xaa = Ala or Pro

<400> SEQUENCE: 51

Gly Val Asp Lys Xaa Gly
 1               5

<210> SEQ ID NO 52
<211> LENGTH: 8
<212> TYPE: PRT
<213> ORGANISM: Artificial Sequence
<220> FEATURE:
<223> OTHER INFORMATION: synthetic
<220> FEATURE:
<221> NAME/KEY: VARIANT
<222> LOCATION: 1
<223> OTHER INFORMATION: Xaa = Ala or Pro
<220> FEATURE:
<221> NAME/KEY: VARIANT
<222> LOCATION: 6
<223> OTHER INFORMATION: Xaa = Ser or Glu
<220> FEATURE:
<221> NAME/KEY: VARIANT
<222> LOCATION: 7
<223> OTHER INFORMATION: Xaa = Val or Lys
<220> FEATURE:
<221> NAME/KEY: VARIANT
<222> LOCATION: 8
<223> OTHER INFORMATION: Xaa = Asp or Asn

<400> SEQUENCE: 52

```
Xaa Phe Gly Gly Cys Xaa Xaa Xaa
 1               5
```

<210> SEQ ID NO 53
<211> LENGTH: 5
<212> TYPE: PRT
<213> ORGANISM: Artificial Sequence
<220> FEATURE:
<223> OTHER INFORMATION: synthetic
<220> FEATURE:
<221> NAME/KEY: VARIANT
<222> LOCATION: 1
<223> OTHER INFORMATION: Xaa = Asp or Glu

<400> SEQUENCE: 53

```
Xaa Thr Phe Ser Asp
 1               5
```

<210> SEQ ID NO 54
<211> LENGTH: 42
<212> TYPE: PRT
<213> ORGANISM: Artificial Sequence
<220> FEATURE:
<223> OTHER INFORMATION: synthetic
<220> FEATURE:
<221> NAME/KEY: VARIANT
<222> LOCATION: 5
<223> OTHER INFORMATION: Xaa = Ala or Pro
<220> FEATURE:
<221> NAME/KEY: VARIANT
<222> LOCATION: 15
<223> OTHER INFORMATION: Xaa = Ser or Glu
<220> FEATURE:
<221> NAME/KEY: VARIANT
<222> LOCATION: 16
<223> OTHER INFORMATION: Xaa = Val or Lys
<220> FEATURE:
<221> NAME/KEY: VARIANT
<222> LOCATION: 17
<223> OTHER INFORMATION: Xaa = Asp or Asn
<220> FEATURE:
<221> NAME/KEY: VARIANT
<222> LOCATION: 23
<223> OTHER INFORMATION: Xaa = Arg or Lys
<220> FEATURE:
<221> NAME/KEY: VARIANT
<222> LOCATION: 27
<223> OTHER INFORMATION: Xaa = His or Lys
<220> FEATURE:
<221> NAME/KEY: VARIANT
<222> LOCATION: 28
<223> OTHER INFORMATION: Xaa = Ser or Asp
<220> FEATURE:
<221> NAME/KEY: VARIANT
<222> LOCATION: 29
<223> OTHER INFORMATION: Xaa = Ile or Leu
<220> FEATURE:
<221> NAME/KEY: VARIANT
<222> LOCATION: 30
<223> OTHER INFORMATION: Xaa = Phe or Leu
<220> FEATURE:
<221> NAME/KEY: VARIANT
<222> LOCATION: 32
<223> OTHER INFORMATION: Xaa = Tyr or deletion
<220> FEATURE:
<221> NAME/KEY: VARIANT
<222> LOCATION: 37
<223> OTHER INFORMATION: Xaa = Asp or Glu
<220> FEATURE:
<221> NAME/KEY: VARIANT
<222> LOCATION: 38
<223> OTHER INFORMATION: Xaa = Leu or Val
<220> FEATURE:
<221> NAME/KEY: VARIANT
<222> LOCATION: 40
<223> OTHER INFORMATION: Xaa = Phe or Gly

```
<220> FEATURE:
<221> NAME/KEY: VARIANT
<222> LOCATION: 41
<223> OTHER INFORMATION: Xaa = Ser or Glu or deletion
<220> FEATURE:
<221> NAME/KEY: VARIANT
<222> LOCATION: 42
<223> OTHER INFORMATION: Xaa = Phe or Asp or deletion

<400> SEQUENCE: 54

Gly Val Asp Lys Xaa Gly Cys Arg Tyr Met Phe Gly Gly Cys Xaa Xaa
 1               5                  10                  15

Xaa Asp Asp Cys Cys Pro Xaa Leu Gly Cys Xaa Xaa Xaa Xaa Ser Xaa
                20                  25                  30

Tyr Cys Ala Trp Xaa Xaa Thr Xaa Xaa Xaa
                35                  40

<210> SEQ ID NO 55
<211> LENGTH: 36
<212> TYPE: PRT
<213> ORGANISM: Artificial Sequence
<220> FEATURE:
<223> OTHER INFORMATION: synthetic
<220> FEATURE:
<221> NAME/KEY: VARIANT
<222> LOCATION: 9
<223> OTHER INFORMATION: Xaa = Ser or Glu
<220> FEATURE:
<221> NAME/KEY: VARIANT
<222> LOCATION: 10
<223> OTHER INFORMATION: Xaa = Val or Lys
<220> FEATURE:
<221> NAME/KEY: VARIANT
<222> LOCATION: 11
<223> OTHER INFORMATION: Xaa = Asp or Asn
<220> FEATURE:
<221> NAME/KEY: VARIANT
<222> LOCATION: 17
<223> OTHER INFORMATION: Xaa = Arg or Lys
<220> FEATURE:
<221> NAME/KEY: VARIANT
<222> LOCATION: 21
<223> OTHER INFORMATION: Xaa = His or Lys
<220> FEATURE:
<221> NAME/KEY: VARIANT
<222> LOCATION: 22
<223> OTHER INFORMATION: Xaa = Ser or Asp
<220> FEATURE:
<221> NAME/KEY: VARIANT
<222> LOCATION: 23
<223> OTHER INFORMATION: Xaa = Ile or Leu
<220> FEATURE:
<221> NAME/KEY: VARIANT
<222> LOCATION: 24
<223> OTHER INFORMATION: Xaa = Phe or Leu
<220> FEATURE:
<221> NAME/KEY: VARIANT
<222> LOCATION: 26
<223> OTHER INFORMATION: Xaa = Tyr or deletion
<220> FEATURE:
<221> NAME/KEY: VARIANT
<222> LOCATION: 31
<223> OTHER INFORMATION: Xaa = Asp or Glu
<220> FEATURE:
<221> NAME/KEY: VARIANT
<222> LOCATION: 32
<223> OTHER INFORMATION: Xaa = Leu or Val
<220> FEATURE:
<221> NAME/KEY: VARIANT
<222> LOCATION: 34
<223> OTHER INFORMATION: Xaa = Phe or Gly
<220> FEATURE:
<221> NAME/KEY: VARIANT
<222> LOCATION: 35
<223> OTHER INFORMATION: Xaa = Ser or Glu or deletion
```

-continued

```
<220> FEATURE:
<221> NAME/KEY: VARIANT
<222> LOCATION: 36
<223> OTHER INFORMATION: Xaa = Phe or Asp or deletion

<400> SEQUENCE: 55

Cys Arg Tyr Met Phe Gly Gly Cys Xaa Xaa Xaa Asp Asp Cys Cys Pro
 1               5                  10                  15

Xaa Leu Gly Cys Xaa Xaa Xaa Xaa Ser Xaa Tyr Cys Ala Trp Xaa Xaa
            20                  25                  30

Thr Xaa Xaa Xaa
        35

<210> SEQ ID NO 56
<211> LENGTH: 42
<212> TYPE: PRT
<213> ORGANISM: Artificial Sequence
<220> FEATURE:
<223> OTHER INFORMATION: synthetic
<220> FEATURE:
<221> NAME/KEY: VARIANT
<222> LOCATION: 10
<223> OTHER INFORMATION: Xaa = Ile or Val or Leu
<220> FEATURE:
<221> NAME/KEY: VARIANT
<222> LOCATION: 15
<223> OTHER INFORMATION: Xaa = Ser, Thr, Pro, 4Hyp, Ala, or Gly
<220> FEATURE:
<221> NAME/KEY: VARIANT
<222> LOCATION: 16
<223> OTHER INFORMATION: Xaa = His, Arg, Lys, Ile, Val, Leu or Met
<220> FEATURE:
<221> NAME/KEY: VARIANT
<222> LOCATION: 17
<223> OTHER INFORMATION: Xaa = Asn, Asp, Glu, or Gln
<220> FEATURE:
<221> NAME/KEY: VARIANT
<222> LOCATION: 27
<223> OTHER INFORMATION: Xaa = Asn, Asp, Glu, Gln, His, Arg, Lys, or
      deletion
<220> FEATURE:
<221> NAME/KEY: VARIANT
<222> LOCATION: 28
<223> OTHER INFORMATION: Xaa = His, Arg, Lys, Ile, Val, Leu or Met
<220> FEATURE:
<221> NAME/KEY: VARIANT
<222> LOCATION: 29
<223> OTHER INFORMATION: Xaa = Ser, Thr, Pro, 4Hyp, Ala, Gly, His, Arg,
      or Lys
<220> FEATURE:
<221> NAME/KEY: VARIANT
<222> LOCATION: 30
<223> OTHER INFORMATION: Xaa = Ser, Thr, Pro, 4Hyp, Ala, Gly, Ile, Val,
      Leu or Met
<220> FEATURE:
<221> NAME/KEY: VARIANT
<222> LOCATION: 31
<223> OTHER INFORMATION: Xaa = Phe, Tyr, or Trp
<220> FEATURE:
<221> NAME/KEY: VARIANT
<222> LOCATION: 32
<223> OTHER INFORMATION: Xaa = Ser, Thr, Pro, 4Hyp, Ala, Gly, Asn, Asp,
      Glu, or Gln
<220> FEATURE:
<221> NAME/KEY: VARIANT
<222> LOCATION: 38
<223> OTHER INFORMATION: Xaa = Ser, Thr, Pro, 4Hyp, Ala, Gly, Ile, Val,
      Leu, Met, Phe, Tyr, or Trp
```

```
<400> SEQUENCE: 56

Gly Val Asp Lys Ala Gly Cys Arg Tyr Xaa Phe Gly Gly Cys Xaa Xaa
 1               5                  10                  15

Xaa Asp Asp Cys Cys Pro Arg Leu Gly Cys Xaa Xaa Xaa Xaa Xaa Xaa Tyr
            20                  25                  30

Cys Ala Trp Asp Xaa Thr Phe Ser Asp
 35                  40
```

VOLTAGE-GATED CALCIUM CHANNEL ANTAGONIST AND METHOD

This application is a divisional of U.S. application Ser. No. 08/904,431, filed Aug. 1, 1997, now U.S. Pat. No. 6,156,726, which claims the benefit of U.S. Provisional Application No. 60/022,978 filed Aug. 2, 1996, both of which are incorporated herein by reference.

FIELD OF THE INVENTION

The present invention relates to a novel class of peptide compounds that specifically block class E voltage-gated calcium channels and to methods for blocking such channels. The invention also, relates to therapeutic treatments, such as treatment of convulsive disorders, using the compounds.

REFERENCES

Banga, A. K., Therapeutic Peptides and Proteins. Technomic Publishing Inc., Lancaster, Pa. (1995).
Biel, M., et al., *FEBS Lett.* 269:409–412 (1990).
Bruckner, H., et al., *J. Chromatog.* 476:73–82 (1989).
Carbone, E., et al., *Pflugers Arch.* 416:170–179 (1990).
Cohen, C. J., et al., *Mol Pharmacol.* 42:947–951 (1994).
Ellinor, P. T., et al., *Nature* 372(6503):272–275 (1994).
Ellis, et al., *Science* 241 (4873):1661–1664 (1988).
Ertel, E. A., et al., *Biochemistry* 33:5098–5108 (1994).
Forti, L., et al., *J. Neurosci.* 14:5243–5256 (1994).
Frohman, M. A., et al., *Proc. Natl. Acad. Sci. USA* 85:8998–9002 (1988).
Frohman, M. A., in *PCR PROTOCOL: A GUIDE TO METHODS AND APPLICATIONS*, Academic Press, New York, N.Y., p. 28 (1990).
Fujita, Y., et al., *Neuron* 10:585 (1993).
Hamil, O. P., et al., *Pflugers Archiv.* 391: 85–100 (1981).
Grynkiewicz, G., et al., *J. Biol. Chem.* 260:3440–3450 (1985)
Hagiwara, K., et al., *Biomed. Res.* 11:181–186 (1990).
Hamill, O. P., et al., *Pflugers Arch.* 391:85–100 (1981).
Hawke, D., and Yuan, P., *Appl. Biosystems User Bull.* 28:1–8 (1987).
Hillyard, et al., *Neuron* 9:69–77 (1993).
Horne, W. A., et al., PCT/US94/08589 (WO 95/04144) (1995).
Jackson, H. C. and Scheideler, M. A. Psychopharmacology 126: 85–90, 1996.
Lampe, R. A., et al., *Mol. Pharmacol.* 44:451–460 (1993).
Lievano, A., et al., *Am. J. Physiol.* 267 (Cell Physiol.) :C411–C424 (1994).
Llinas, R., et al., Trends Neurosci. 15:351–354 (1992).)
Maniatis, T., et al., *MOLECULAR CLONING: A LABORATORY MANUAL*, Cold Spring Harbor Laboratory, Cold Spring Harbor, N.Y. (1982).
Mikami, A. et al., *Nature* 340:230–233(1989).
Mori, Y., et al., *Nature* 350:398–402 (1991).
Newcomb, R., et al., *Biochemistry* 34:8341–8347 (1995).
Newcomb, R., et al., *LC-GC Mag. Sep. Sci.* 7: 570–578 (1989).
Palma, A., et al., *Soc. Neurosci. Abstr.* 20(1–2) (1994).
Perez-Reyes, E., et al., *Nature* 340:233–236 (1989)
Piser, T. M., et al., *Mol. Pharmacol.* 48:131–139 (1995).
Premack, A. B., et al., *J. Immunol.* 152:5226–5240 (1994).
Rae, J., et al., J. Neurosci. Meth. 87:15 (1991).
Ramaswami, M., et al., *Mol. Cell. Neurosci.* 1:214–223 (1990).
Randall, A., and Tsien, R. W., *J. Neurosci.* 15:2995–3012 (1995).
Sather, W. A., et al., *Neuron* 11:291–303 (1993).
Smith, P. K., et al., *Anal. Biochem.* 150:76 (1985).
Snutch, T. P., et al., *Proc. Natl. Acad. Sci.* 87:3391–3395 (1990).
Soong, T. W., et al., *Science* 260:1133–1136 (1993).
Stea, A., et al., *Proc. Natl. Acad. Sci.* 91:10576–10580 (1994).
Swartz, K. J., and MacKinnon, R., *Neuron* 15:941–949 (1995).
Tanabe, T., et al., *Nature* 328:313–318 (1987).
Tarr, G. E., et al., *Proc. Natl. Acad. Sci. USA* 80:6552–6556 (1993).
Tempel, B. L., et al., *Nature* 332:.837–839 (1988).
Tsien, R. W., et al., *Trends Neurosci.* 12:349–354
Venema, V. J., et al., *J. Biol. Chem.* 267:.2610–2615 (1992).
Wang, J., et al. *J. Physiology*, in press.
Williams, M. E., et al., *Neuron* 8:71–84 (1992).
Yaksch, T. L., and Rudy, T. A., *Physiol. Behav.* 17:1031–1036 (1976).

BACKGROUND OF THE INVENTION

Voltage-gated calcium channels are present in neurons, and in cardiac, smooth, and skeletal muscle and other excitable cells. These channels are known to be involved in membrane excitability, muscle contraction, and cellular secretion, such as in exocytotic synaptic transmission. In neuronal cells, voltage-gated calcium channels have been classified by their electrophysiological as well as by their biochemical and pharmacological properties. More recently, further classification has been made based on the molecular biology of the channels. Calcium channels are generally classified according to their electrophysiological properties as Low-voltage-activated (LVA) or High-voltage-activated (HVA) channels. HVA channels are currently known to comprise at least three groups of channels, known as L-, N- and P/Q-type channels. These channels have been distinguished one from another electrophysiologically as well as bio-chemically on the basis of their pharmacology and ligand binding properties. Thus, dihydropyridines, diphenyl-alkylamines and piperidines bind to the alpha$_1$ subunit of the L-type calcium channel and block a proportion of HVA calcium currents in neuronal tissue, which are termed L-type calcium currents. N-type calcium channels are sensitive to omega conopeptides, but are relatively insensitive to dihydropyridine compounds, such as nimodipine and nifedipine. P/Q-type channels, on the other hand, are insensitive to dihydropyridines, but are sensitive to the funnel web spider toxin Aga IIIA.

R-type calcium channels, like L-, N-, P- and Q-type channels, are activated by large membrane depolarizations, and are thus classified as high voltage-activated (HVA) channels. R-type channels are insensitive to dihydropyridines and omega conopeptides, but, like P/Q, L and N channels, are sensitive to the funnel web spider toxin AgaIVA. Immunocytochemical staining studies indicate that these channels are located throughout the brain, particularly in deep midline structures (caudate-putamen, thalamus, hypothalamus, amygdala, cerebellum) and in the nuclei of the ventral midbrain and brainstem. This channel is thought to reside primarily in neuronal cell bodies and dendrites, where it contributes to cellular electrical activity. There is now also evidence that R-type channels may be localized on pre-synaptic nerve terminals.

The molecular complex comprising neuronal voltage-sensitive calcium channels consists of a central $\alpha_1$ subunit, an $\alpha_2/\delta$ subunit, a $\beta$ subunit and a 95 kD subunit. Molecular genetic studies have revealed at least five mRNA classes that code for $\alpha_1$ subunits, designated A, B, C, D, and E. These correspond to the P/Q-type ($\alpha_{1A}$), N-type ($\alpha_{1B}$), L-type ($\alpha_{1C}$, $\alpha_{1D}$), and R-type ($\alpha_{1E}$) voltage-gated channels, as defined by electrophysiological studies. (Snutch et al. 1990, Soong et al. 1993, Tsien et al. 1991; Biel et al. 1990, Mikami et al. 1989, Perez-Reyes et al. 1989, Tanabe et al., Williams et al., 1992; Fujita et al. 1993; Mori et al. 1991, Sather et al. 1993, Stea et. al. 1994 Forti et al. 1994, Randall and Tsien 1994). The class E voltage-gated calcium channel encompasses currents characterized electrophysiologically as R-type and G2 currents.

There are no known specific or selective ligands for the Class E or R-type neuronal calcium channel. Although the spider peptide omega-Aga IIIA antagonizes this channel, it also potently blocks N, P/Q- and L-type calcium currents (Cohen et al. 1993, Ertel et al. 1994) and therefore lacks specificity. The lack of specific ligands for the channel has heretofore impeded elucidation of its role(s) in neuronal function. Table 1 summarizes antagonists of the various subtypes of voltage-gated calcium channels referred to herein.

TABLE 1

| Electrophysiological Class | C-DNA Class | Peptide Ligands |
| --- | --- | --- |
| N-type | B | MVIIA (SNX-111) |
|  |  | GVIA (SNX-124) |
|  |  | MVIIC (SNX-230) |
|  |  | SIA |
|  |  | AGAIIIA |
| P/Q-type | A | MVIIC |
|  |  | SIA |
|  |  | AGAIIIA |
|  |  | AGAIVA |
| T-type | ? | None |
| R-type | E | AGAIIIA |
|  |  | SNX-482 |
| L-type | C | AGAIIIA (?) |
| ? | D | AGAIIIA (?) |

In view of the importance of specific calcium channels in neuronal function, it would be useful to identify pharmacological agents that specifically block the class E calcium channel. The present invention is based on the discovery of a new class of peptides that selectively block this channel. This class of compounds is exemplified herein by the novel HG peptides described herein that are derived from peptides originally isolated from *H. gigas*.

SUMMARY OF THE INVENTION

The present invention relates to a novel class of peptides that selectively block class E calcium channels. More specifically, such peptides, generally referred to as class E voltage-gated calcium channel blocking peptides herein, are capable of blocking class E voltage-sensitive calcium channels at a concentration that is about 10–50, and more preferably no more than 10–20, times the concentration of HG-1 peptide (SEQ ID NO: 1) required to block such channels. The peptides may be further characterized, in another embodiment, by an inability of the particular peptide to block by at least 50% L-type, T-type, P/Q-type or N-type calcium channels, as described herein, at a molar concentration that is about 10 times the molar concentration required to half maximally block a class E voltage-gated calcium channel.

In a preferred embodiment, the peptide takes the form: $V_1$-SEQ ID NO: 19-$X_2X_3X_4$-SEQ ID NO: 20-$X_5$-LGC-$X_6X_7X_8X_9$-S-$X_{10}$-SEQ ID NO: 10-$X_{11}X_{12}$-T-$X_{13}X_{14}X_{15}$ where $V_1$ is GVDKX$_1$G or deletion, $X_1$ being A or P; $X_2$ is S or E, $X_3$ is V or K, $X_4$ is D or N, $X_5$ is R or K, $X_6$ is H or K, $X_7$ is S or D, $X_8$ is I or L, $X_9$ is F or L, $X_{10}$ is Y or deletion, $X_{11}$ is D or E, $X_{12}$ is L or V, $X_{13}$ is F or G, $X_{14}$ is S or E or deletion, and $X_{15}$ is F or D or deletion.

In another preferred embodiment, the peptide has the form: SEQ ID NO: 16-$X_1$-FGGC-$X_2X_3X_4$-SEQ ID NO: 17-$X_5X_6X_7X_8X_9X_{10}$-SEQ ID NO: 18-$X_{11}$-TFSD, wherein $X_1$ is selected from Class V; $X_2$ is selected from Class II; $X_3$ is selected from Class IV or V; $X_4$ is selected from Class III; $X_5$ is selected from Class III or Class IV or deletion; $X_6$ is selected from Class IV or V; $X_7$ is selected from Class II or IV; $X_8$ is selected from Class II or V; $X_9$ is selected from Class VI; $X_{10}$ is selected from Class II or III; and $X_{11}$ is selected from Class II, V or VI. In further preferred embodiment, the variable positions in the above composite peptide assume the following substituents: $X_1$=M or L; $X_2$=S or T; $X_3$=V, K or R; $X_4$=N or D; $X_5$=K, Q or a deletion; $X_6$=H, R, or L; $X_7$=S or K; $X_8$=L or G; $X_9$=F or Y; $X_{10}$=S or N; and $X_{11}$=L, F, or G. In still another preferred embodiment, the peptide is any of SEQ ID NO: 1 (HG-1), SEQ ID NO: 8 (HG-8), SEQ ID NO: 13 (R9), SEQ ID NO: 14 (R11), and SEQ ID NO: 15 (SNX-629).

In another embodiment, the invention includes isolated polynucleotides, comprising, a sequence of nucleotides that encode a peptide selected from the peptides having the sequences defined by SEQ ID NO: 1, SEQ ID NO: 2, SEQ ID NO: 3, SEQ ID NO: 4, SEQ ID NO: 6, SEQ ID NO: 7, SEQ ID NO: 8, SEQ ID NO: 9, SEQ ID NO: 11, SEQ ID NO: 12, SEQ ID NO: 13, SEQ ID NO: 14, and SEQ ID NO: 15. In another embodiment, the polynucleotide is selected from nucleotides having sequences defined by SEQ ID NO: 23 to SEQ ID NO: 43.

In still a further embodiment, the isolated polynucleotide comprises a sequence of nucleotides that encodes a peptide having the sequence: $V_1$-SEQ ID NO: 19-$X_2X_3X_4$-SEQ ID NO: 20-$X_5$-LGC-$X_6X_7X_8X_9$-S-$X_{10}$-SEQ ID NO: 10-$X_{11}X_{12}$-T-$X_{13}X_{14}X_{15}$ where $V_1$ is GVDKX$_1$G SEQ ID NO: 51 or deletion, $X_1$ being A or P; $X_2$ is S or E, $X_3$ is V or K, $X_4$ is D or N, $X_5$ is R or K, $X_6$ is H or K, $X_7$ is S or D, $X_8$ is I or L, $X_9$ is F or L, $X_{10}$ is Y or deletion, $X_{11}$ is D or E, $X_{12}$ is L or V, $X_{13}$ is F or G, $X_{14}$ is S or E or deletion, and $X_{15}$ is F or D or deletion.

In another embodiment, the isolated polynucleotide encodes a peptide having the sequence SEQ ID NO: 16-$X_1$FGGC-$X_2X_3X_4$-SEQ ID NO: 17-$X_5X_6X_7X_8X_9X_{10}$-SEQ ID NO: 18-$X_{11}$-TFSD, wherein $X_1$ is selected from Class V; $X_2$ is selected from Class II; $X_3$ is selected from Class IV or V; $X_4$ is selected from Class III; $X_5$ is selected from Class III or Class IV or deletion; $X_6$ is selected from Class IV or V; $X_7$ is selected from Class II or IV; $X_8$ is selected from Class II or V; $X_9$ is selected from Class VI; $X_{10}$ is selected from Class II or III; and $X_{11}$ is selected from Class II, V or VI.

In a related aspect, the invention includes a method of inhibiting seizures in a subject. The method includes administering to the subject a pharmaceutically effective dose of an HG peptide capable of blocking a class E voltage-gated calcium channel at a concentration that is at most about 10–50 times the concentration of HG-1 peptide (SEQ ID NO: 1) required to block said channel.

In a related embodiment, the peptide used in the anticonvulsive treatment method is further characterized by inability to block by at least 50% L-type, T-type, class A (P/Q type) or class B (N-type) calcium channels at a concentration that is at most about 10-times the concentration required to half maximally block said class E Voltage-gated calcium channel. A preferred peptide for use in this method has the sequence: $V_1$-SEQ ID NO: 19-$X_2X_3X_4$-SEQ ID NO: 20-$X_5$-LGC-$X_6X_7X_8X_9$-S-$X_{10}$ SEQ ID NO: 10-$X_{11}X_{12}$-T-$X_{13}X_{14}X_{15}$ where $V_1$ is GVDK$X_1$G (SEQ ID NO: 51) or deletion, $X_1$ being A or P; $X_2$ is S or E, $X_3$ is V or K, $X_4$ is D or N, $X_5$ is R or K, $X_6$ is H or K, $X_7$ is S or D, $X_8$ is I or L, $X_9$ is F or L, $X_{10}$ is Y or deletion, $X_{11}$ is D or E, $X_{12}$ is L or V, $X_{13}$ is F or G, $X_{14}$ is S or E or deletion, and $X_{15}$ is F or D or deletion. Preferred peptides for use in this method include SEQ ID NO: 1 and SEQ ID NO: 15.

In a further related aspect, the invention includes methods of inhibiting release of neurohypophysial hormones, such as oxytocin, into circulation. Such a method can be employed, for example, to prevent premature labor or to inhibit the let-down response of lactation. The method includes administration of a class E channel blocking HG peptide in an appropriate pharmaceutical excipient. In addition to the HG-peptides which block class E channels, as discussed herein, this treatment paradigm may include administering an L-type calcium channel blocker, an N-type calcium channel blocker or a P/Q type calcium channel blocking agent. An effective therapeutic regimen, in this context, is one in which premature labor is abolished. Such a regimen may also be used to inhibit the lactation let-down response in a lactating female.

The invention also includes methods of selecting compounds for use in the foregoing treatment methods (inhibition of prolactin release, anticonvulsant activity). The method includes testing a compound for ability to selectively block class E calcium channels in neuronal tissue, and selecting the compound it blocks calcium currents through said class E calcium channels at a concentration that is no more than about 10–50 times a concentration of HG-1 peptide effective to block said currents.

In a related embodiment, the invention includes a method for selecting compounds for use in treating disorders, such as epilepsy or oversecretion of oxytocin, in which blockade of class E calcium channels is indicated. The selection method includes testing the compound in an assay system that measures class E channel activity and selecting the compound if it blocks calcium currents through such channels at a concentration that is no more than about 50 times a concentration of HG-1 peptide that is effective to block such channels. An exemplary screening assay is the whole-cell patch clamp of neurohypophysial terminals described herein. The selection method may, in addition, utilize additional screens, such as N-, L-, or P/Q-type calcium channel assays, to ensure that the selected compound is selective for class E channels.

In another aspect, the invention includes recombinant methods for producing class E voltage-gated calcium channel blocking peptides. In particular, for use in such a method, the invention includes the nucleotide fragments having the sequences: SEQ ID NOs: 23 to SEQ ID NO: 43.

These and other objects and features of the invention will become more fully apparent when the following detailed description of the invention is read in conjunction with the accompanying drawings.

BRIEF DESCRIPTION OF THE FIGURES

FIGS. 1(A–C) show an HPLC profile of (A) elution of crude venom from Hysterocrates gigas, (B) rechromatography of the peak from panel A, and (C) rechromatography of the peak from panel B, where the arrow in each case indicates the HG-1 peak;

FIG. 2A shows a comparison of the amino acid sequences of HG-1 (SEQ ID NO: 1), HG-2 (SEQ ID NO: 2), HG-3 (SEQ ID NO: 3), R1 (SEQ ID NO: 11) R2 (SEQ ID NO: 12), R9 (SEQ ID NO: 13), and R11 (SEQ ID NO: 14), aligned to show conserved regions and cysteine residues.

FIG. 2B shows HG-1 (SEQ. ID NO: 1), HG-2 (SEQ ID NO: 2), HG-6 (SEQ ID NO: 6), HG-7 (SEQ ID NO: 7) and HG-8 (SEQ ID NO: 8) aligned to show conserved regions;

FIG. 2C shows propeptides of HG-1 (SEQ ID NO: 48), HG-2 (SEQ ID NO: 49), HG-8 (SEQ ID NO: 21) and HG-4 (SEQ ID NO: 22) aligned to show conserved regions;

FIG. 2D shows HG-1 (SEQ ID NO: 1), HG-2 (SEQ ID NO: 2), HG-6 (SEQ ID NO: 6), HG-7 (SEQ ID NO: 7), HG-9 (SEQ ID NO: 9), HG-8 (SEQ ID NO: 8) and HG-4 (SEQ ID NO: 4) aligned to show conserved regions;

FIG. 2E shows a comparison of the amino acid sequences HG-1 (SEQ ID NO: 1), HG-2 (SEQ ID NO: 2) and HG-3 (SEQ ID NO: 3) aligned to show conserved and variable regions $V_1$–$V_4$ (boldface).

FIG. 2F shows a comparison of HG-1 (SEQ ID NO: 48), R9 (SEQ ID NO: 13), R11 (SEQ ID NO: 14), H-G (SEQ ID NO: 8) and SNX-629 (HG-1 (7–41); SEQ ID NO: 15);

FIG. 3 shows a comparisons of the sequence of HG-1 (SEQ ID NO: 1) to the peptides grammatoxin S1A (SEQ ID NO: 45) (Lampe et al. 1993), and hanatoxin (SEQ ID NO: 44) with aligned cysteine residues;

FIGS. 4A–4G shows coding sequences for HG-1 (SEQ ID NO: 23 (leader), SEQ ID NO: 24 (coding) and SEQ ID NO: 25 (entire sequence shown)), HG-2 (SEQ ID NO: 26 (leader), SEQ ID NO: 27 (coding) and SEQ ID NO: 28 (entire sequence shown)), HG-3 (SEQ ID NO: 29 (leader), SEQ ID NO: 30 (coding) and SEQ ID NO: 31 (entire sequence shown)), HG-4 (SEQ ID NO: 32 (leader) SEQ ID NO: 33 (coding) and SEQ ID NO: 34 (entire sequence shown)), HG-4 (SEQ ID NO: 35 (leader), SEQ ID NO: 36 (coding) and SEQ ID NO 37 (entire sequence shown)), HG-6 (SEQ ID NO: 38) (leader), SEQ ID NO: 39 (coding) and SEQ ID NO: 40 (entire sequence shown)), and HG-9 (SEQ ID NO: 41 (leader), SEQ ID NO: 42 (coding) and SEQ ID NO 43 (entire sequence shown)), where, in each sequence the beginning of the leader sequence is indicated with a line and the letter "L", the beginning of the mature peptide coding region is indicated by a line and an arrow, and the end of the coding sequence is indicated with a third line;

FIG. 5 shows the waveform of a calcium current in whole cell patch clamp (192C cell) in the presence and absence of 33 nM HG-1, as indicated;

FIG. 6 shows the effects of varying concentrations of HG-1 on peak inward calcium current in cells stably expressing Class E (192C) and Class B (S-3) type alpha-1 subunits and the effects of Aga IIIA on 192C cells expressing the class E alpha-1 subunit;

FIG. 7 shows the effects of nicardipine, omega conotoxin MVIIA (SNX-111), omega conotoxin MVIIC (SNX-230)

and HG-1 (SNX-482) on the calcium current (carried by barium) in neurohypophyseal terminals;

FIGS. 8(A–C) show concentration-effect curves for various compounds on internal calcium concentration subsequent to potassium depolarization as measured by fluorescence ratio of cells treated with the calcium sensitive dye INDO-1: (A) on 192C cells expressing class E channels, the effects of HG-1 and Aga-IIIA; (B) on GH3 cells which have both L-type and T-type calcium channels, the effects of HG-1, Aga-IIIA, and nitrendipine, where the inset shows a typical time course of INDO-1 fluorescence in cells subjected to potassium depolarization in the absence and presence of 5 $\mu$M nitrendipine; (C) on IMR-32 neuroblastoma cells which exhibit primarily N-type calcium channels, the effects of HG-1, Aga-IIIA and SNX-194 (met-12 to norleu-12-SNX-111); and FIGS. 9A and 9B show the effects of varying doses of SNX-482 (HG-1) on convulsive behaviors in DBA/2 mice subjected to audiogenic stimuli;

DETAILED DESCRIPTION OF THE INVENTION

Definitions

Figure 1A:
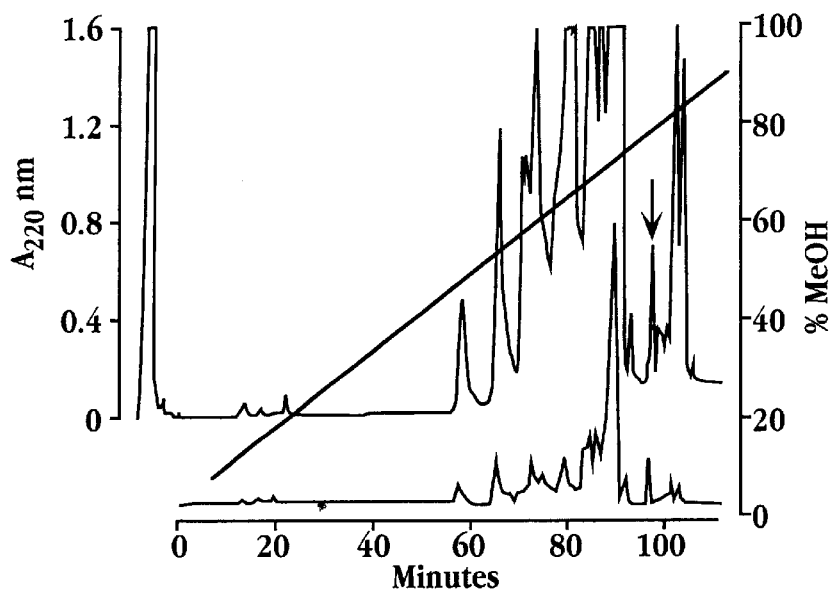

The term "polynucleotide" as used herein refers to a polymeric molecule having a backbone that supports bases capable of hydrogen bonding to typical polynucleotides, where the polymer backbone presents the bases in a manner to permit such hydrogen bonding in a sequence specific fashion between the polymeric molecule and a typical polynucleotide (e.g., single-stranded DNA). Such bases are typically inosine, adenosine, guanosine, cytosine, uracil and thymidine. Polymeric molecules include double and single stranded RNA and DNA, and backbone modifications thereof, for example, methylphosphonate linkages.

The term "vector" refers to a nucleotide sequence that can assimilate new nucleic acids, and propagate those new sequences in an appropriate host. Vectors include, but are not limited to recombinant plasmids and viruses. The vector (e.g., plasmid or recombinant virus) comprising the nucleic acid of the invention can be in a carrier, for example, a plasmid complexed to protein, a plasmid complexed with lipid-based nucleic acid transduction systems, or other non-viral carrier systems.

The term "polypeptide" as used herein refers to a compound made up of a single chain of amino acid residues linked by peptide bonds. The term "protein" may be synonymous with the term "polypeptide" or may refer, in addition to a complex of two or more polypeptides.

As used herein, the terms "substantial homology" or "substantial identity", and declinations thereof, refer to concordance of an amino acid sequence with another amino acid sequence or of a polynucleotide sequence with another polynucleotide sequence of at least 70% and preferably, at least about 80% or greater, when such sequences are arranged in a best fit alignment. In the case of nucleotide sequences, the terms also imply that the nucleotide sequence in question is capable of being detected in a screening assay by a hybridization probe derived from a specified polynucleotide sequence.

I. Class E Voltage-gated Calcium Channel Blocking Peptides

This section describes the novel class of peptides that are the subject of the present invention, focusing on their structural characteristics. Class E voltage-gated calcium channel blocking peptides, which are variously referred to herein as HG peptides, or as HG-1 derivatives or analogs, are defined on the basis of their structures, and further on the basis of their in vitro calcium channel blocking specificities, as described in Section II, below.

A. Isolation of Class E Voltagae-gated Calcium Channel Blocking Peptides

HG peptides can be identified and isolated according to a number of methods that employ standard art techniques. Principally, such methods include biochemical purification from natural sources, isolation and/or identification of nucleotide coding sequences, and synthetic or recombinant manufacture of the characterized molecule. While in the examples below, the "natural source" is the venom gland of a particular species of tarantula, it is appreciated that the isolation and or identification techniques described herein can be applied more generally to tarantulas, as well as to other spiders and organisms. These methods are illustrated by example below.

1. Purification of HG-1 From *Hysterocrates gigas* Venom.

It is the discovery of the present invention that peptides selective for class E calcium channels can be identified in and isolated from the venoms of Old World and New World tarantulas such as *H. gigas*. These peptides are relatively acidic at neutral pH and are also relatively hydrophobic. Thus, they are conveniently isolated by techniques which exploit these properties. These techniques are generally, described by Newcomb, et al. (1989).

Example 1 provides exemplary methods that can be used to purify HG-1 from *H. gigas* venom. Briefly, the spider venom is collected according to standard "milking" techniques and is flash frozen until use. The thawed sample is applied to an HPLC column, as detailed in Example 1. Elution is monitored by absorbance at 220 nm and by endogenous fluorescence, according to standard techniques. A linear gradient of methanol in 12 mM sodium phosphate (pH 6.2) of 0–100% over 125 min. at 1 mL/min provides good separation of the venom components.

Figure 1B:
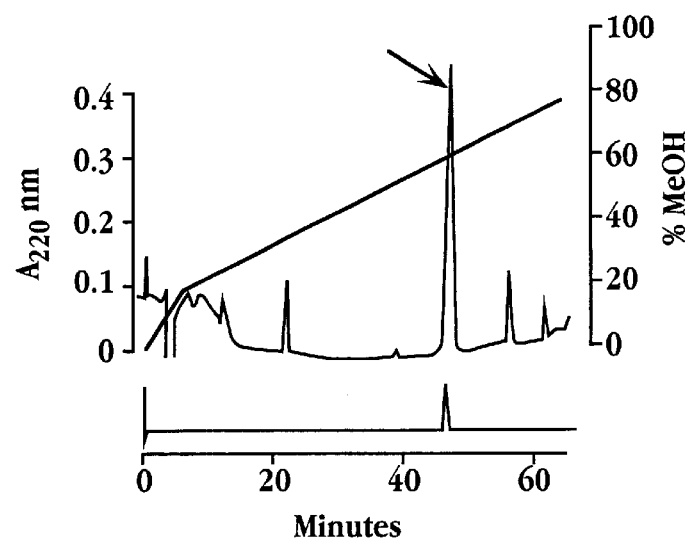
Figure 1C:
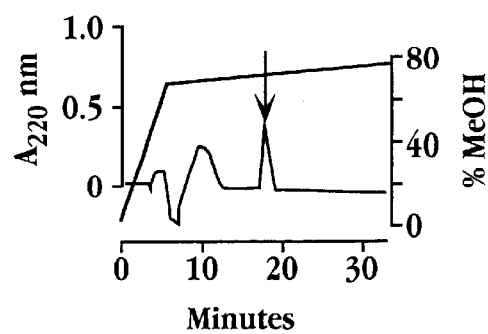

FIG. 1A shows the absorbance ($A_{220}$; upper trace) and fluorescence (lower trace) patterns produced by elution of an HPLC column onto which had been loaded the crude venom of *H. gigas*, as detailed in Example 1. The arrow represents, the peak of HG-1 activity, assessed by electrophysiological measurements made on 192C cells (HEK cells stably transfected with the Class E channel), as described in Example 6. FIG. 1B shows the elution profile obtained when the peak from panel A was re-chromatographed using an aqueous buffer of 0.1% TFA, and FIG. 1C shows the pattern obtained after re-chromatography of the peak from panel B, eluted with an aqueous buffer of 0.05% HFBA.

Edman degradation, as well as amino acid analysis of those amino acids not present in the active, HG-1-containing fraction (glu and ile) showed the TFA purified material (active peak in panel B) to be 95–99% pure (with the early eluting part of the peak being of greater purity). The active material from this separation was rechromatographed using an aqueous buffer of 0.05% heptafluorobutyric acid (HFBA) (0–65% methanol over 5 minutes, followed by 65–85% over 50 minutes; FIG. 1C). This material was of 99% or greater purity, by Edman degradation and amino acid analysis.

Using the methods described above, the venom of *H. gigas* reproducibly yielded material that eluted at between 70–80% methanol and antagonized the class E calcium current. Further purification was obtained by reversed phase chromatography at acidic pH using aqueous buffers of 0.1% TFA followed by 0.05% HFBA. Bioassay of 1 mL fractions showed that the class E calcium antagonist co-chromatographed with the predominant material on both of these solvent systems (Arrows, FIGS. 1B and 1C); as measured both by whole cell patch clamp as well as through depolarization evoked changes in internal calcium concentrations. The purified natural product was denoted HG-1. The amino acid content and sequence of this peptide are discussed in sub-section 2, below.

2. Determination of Structure of HG-1.

The purified HG-1 peptide was subjected to matrix assisted laser desorption mass spectrometry. From this procedure, an approximate molecular mass of 4500 was measured for HG-1, while the presence of endogenous fluorescence indicated the presence of tryptophan. Based on these results and the results of amino acid analysis (Example 3), an amino acid composition was determined as shown in Table 2. In the table, amino acids are indicated by conventional 3-letter identifiers and are listed as DL in cases where the two enantiomers were not resolved by the analysis (his), or they were not detected in the amino acid analysis (pro and cys).

TABLE 2

AMINO ACID COMPOSITION OF HG-1

| Amino Acid | Residues | Std. Dev. | Sequence |
| --- | --- | --- | --- |
| L-Asp (+Asn) | 6.37 | 0.39 | 5 (+1) |
| L-Ser | 4.08 | 0.49 | 4 |
| DL-His | 0.98 | 0.10 | 1 |
| Gly | 4.29 | 0.51 | 5 |
| L-Arg | 2.02 | 0.12 | 2 |
| L-Ala | 2.03 | 0.14 | 2 |
| L-Tyr | 2.29 | 0.52 | 2 |
| L-Val | 2.01 | 0.17 | 2 |
| L-Met | + | | 1 |
| L-Trp | 1.1 | | 1 |
| L-Phe | 3.02 | 0.16 | 3 |
| L-Lys | 1.06 | 0.07 | 1 |
| L-Leu | 2.86 | 0.11 | 3 |
| DL-Pro | | | 1 |
| DL-Cys | | | 6 |

Edman degradation of 0.5 nmol of the full length alkylated peptide provided sequence information to position 35, indicating the presence of 6 cysteine residues and a single proline residue. Trypsin was used to cleave two nmol of the alkylated peptide at position 23, and the sequence of the carboxyl-terminal fragment gave the sequence of HG-1 to position 39, while low yields of Ser and Asp (approximately 1 pmol) were obtained at positions 40 and 41. The amino terminal portion of the sequence was verified by sequencing of the remainder of the tryptic fragments, which showed no additional sequence beyond amino acid 41 of HG-1. The carboxyl-terminal. Ser-Asp sequence was verified by digestion with carboxypeptidase A. Both carboxypeptidases A and Y liberated the free carboxyl form of Asp. Of those amino acids for which chirality was determined (i.e., all except gly, pro, cys and his), only the L-enantiomers were detected. The sequence of HG-1 predicts a peptide of molecular mass 4495.10 daltons. This mass is consistent with the mass determined using electrospray mass spectrometry (4494.86±0.11 daltons).

The amino acid sequence of HG-1 is shown in FIG. 2 and is assigned SEQ ID NO: 1.

3. Isolation of Nucleotide Coding Sequences for HG Peptides.

From the HG peptide sequences shown in FIG. 2, oligonucleotide primers can be designed and synthesized, in order to isolate and determine coding sequences for nucleotides that encode the HG peptides illustrated as well as other HG peptides. One useful method for isolating such sequences is the PCR rapid amplification of cDNA ends (PCR-RACE) reaction (Frohman et al. 1988, Frohman 1990) which is detailed in Example 10.

Using HG-1 as an example, 3' oligonucleotide primers were designed and made, based on the N-terminal sequence of HG-1 (e.g., SEQ ID NO: 5) and using insect codon preferences to reduce degeneracy. Poly-A mRNA was isolated from the venom producing cells of 3–5 spiders, and cDNA was produced using the methods described in Example 10. The cDNA was TdT tailed and used as a substrate for PCR using as a 3' primer, a degenerate oligonucleotide primer based on the N-terminal sequence of HG-1. The amplification products were analyzed by agarose gel electrophoresis; on the basis of this analysis, 5' degenerate primers were made and used to obtain non-coding regions at the 5' end of the coding region (e.g., upstream of the coding region that codes for the N terminal portion of the peptide). This method is advantageous for obtaining complete coding regions from a small amount of starting material. Sequences of the isolated fragments were determined according to standard methods known in the art. Exemplary nucleotide sequences are shown in FIGS. 4A–4G. Shown in the figures are leader sequences followed by mature peptide coding regions, as indicated;

The resulting DNA coding segment can be synthesized according to methods known in the art, inserted into an appropriate vector and used to construct peptide producing cells, including, but not limited to yeast cells, insect cells, mammalian cells, plant cells or bacterial cells.

4. Synthesis of Class E Voltage-gated Calcium Channel Blocking Peptides.

HG peptides and HG-1 derivatives can be made by chemical synthetic means or expressed recombinantly using methods known in the art, as described below.

a. Solid Phase Synthesis. Peptides in accord with the present invention can be synthesized by a solid-phase synthesis method using an automated peptide synthesizer, according to methods, known in the art. N-alpha-protected (F-moc) amino acid anhydrides are prepared in crystallized form and used for successive amino acid addition at the N-terminus, utilizing side chain protecting groups, as detailed for HG-1 in Example 12 herein. The synthetic method is based on common art methods, taking into consideration that the HG-1 peptide is acid labile. The peptide is cleaved from the resin and is then further processed (oxidized) in the presence of oxidized and reduced glutathione (1:2 ratio) at pH 9.5, to cause formation of intrachain disulfide linkages in the proper configuration. The progress of the oxidation step can be monitored by analytical HPLC on a C18 column. Preparative purification of the peptide is achieved using the preparative HPLC system (Septech annular expansion column (Septech, Wakefield, R.I.).

The peptide can be isolated by an initial separation by gel filtration, to remove peptide dimers and higher polymers, and also to remove undesired salts, such as guanidine hydrochloride, used in the oxidation reaction. The partially purified peptide is further purified by preparative HPLC chromatography, and the purity of the peptide confirmed by amino acid composition analysis.

The synthetic peptide corresponding to HG-1 is designated SNX-482 (SEQ ID NO: 1). A synthetic peptide corresponding to HG 1 (7–41) is; designated SNX-629 (SEQ ID NO: 15).

b. Recombinant Expression of Class E Voltage-gated Calcium Channel Blocking Peptides. Peptides can be prepared according to recombinant means well known in the art in bacterial, yeast, or preferably, insect cells. According to one general paradigm, cellular DNA is obtained from the venom producing cells of a source spider, such as *H. gigas* and the coding region for HG-1 or an HG-1 analog variant is isolated, as described in sub-section 2, above.

Alternatively, the amino acid coding sequence for HG-1 can be used to generate a corresponding DNA coding sequence with codon usage optimized for expression in the cells of choice (e.g., bacterial, mammalian, yeast or insect cells). The DNA coding sequence is synthetically constructed by sequential addition of oligonucleotides, according to methods known in the art. Cloned oligonucleotides are fused into a single polynucleotide using the usual restriction digestions and ligations.

For expression of recombinant HG-1, this synthetic coding sequence can be placed in any of a number of bacterial expression vectors: for example, lambda gt11 (Promega, Madison Wis.); PGEX (Smith et al., 1985); pGEMEX (Promega); and pBS (Stratagene, La Jolla Calif.) vectors. Other bacterial expression vectors containing suitable promoters, such as the T7 RNA polymerase promoter or the tac promoter, may also be used. For expression in insect cells (*Spodoptera frugiperda*), the coding sequence is inserted into an appropriate baculoviral vector, such as is available from Invitrogen (San Diego, Calif.). Other appropriate expression systems include, but are not limited to mammalian cells (Clontech, Palo Alto Calif.; Gibco-BRL, Gaithersburg Md.), and plant cells.

Recombinant polypeptides can be expressed as fusion proteins or as native proteins. A number of features can be engineered into the expression vectors, such as leader sequences which promote, the secretion of the expressed sequences into culture medium. The recombinantly produced polypeptides are typically isolated from lysed cells or culture media. Purification can be carried out by methods known in the art, including but not limited to, salt fractionation, ion exchange chromatography, and affinity chromatography. Immunoaffinity chromatography can be employed using antibodies generated based on the HG-1 peptide, and particularly the conserved region of the peptide, as discussed in Section B, below.

B. Structural Features of Class E Voltage-gated Calcium Channel Blocking Peptides It is the discovery of the present invention that HG peptides share a pharmacological profile that renders them particularly useful as selective antagonists ("blockers") of class E voltage-gated calcium channels. This section describes what is encompassed by the terms "class E voltage-gated calcium channel blocking peptide", "HG peptide" and "HG-1 derivative or analogs". The term "selective antagonist", as used in the context of the present invention is described and illustrated in Section II, below.

Class E voltage-gated calcium channel blocking peptides are exemplified by HG-1 (SEQ ID NO: 1), as shown in FIG. 2A. As discussed below, a composite HG-peptide can be formed from by comparing the various structures illustrated in FIGS. 2A–2F, designated SEQ ID NO: 1 to SEQ ID NO: 15, taken in conjunction with a comparison to related structures that do not exhibit the desired pharmacological profile, form the basis for the structural constraints of HG peptides.

FIG. 3 shows a comparison of the sequence of HG-1 to that of other spider calcium and potassium antagonist peptides having the same or a similar pattern of cysteine residues (C-C-CC-C-C). As shown, the primary sequence of HG-1 exhibits some homology to the peptides grammatoxin S1A (SEQ ID NO: 45) (Lampe et al. 1993), and hanatoxin (SEQ ID NO: 44) (Swartz and MacKinnon 1995) both isolated from the venom of the tarantula *Grammostola spatulata*. Grammatoxin S1A is a fairly nonselective blocker of N- and P-/Q-, but not L calcium channel subtypes (Lampe et al., 1993; Piser et al, 1995). Hanatoxin is a potassium channel antagonist (Swartz and MacKinnon 1995). It is notable in the context of the present invention that neither of these peptides exhibits class E calcium channel antagonist activity.

From the foregoing, it can be deduced that the cysteine residue pattern of HG-1 and related peptides is necessary but not sufficient to provide the class E calcium channel selectivity that is the hallmark of HG peptides. The structures of these peptides therefore represent peptide sequences which would not fall within the definition of "HG peptides" as defined herein, and therefore provide guidance for "negative selections" within the context of the present invention.

By way of example FIG. 2E shows a comparison of the amino acid sequences of HG-1 (SEQ ID NO: 1) and the deduced amino acid sequence of HG-2 (SEQ ID NO: 2) and HG-3 (SEQ ID NO: 3). By aligning HG-1 and HG-2 such that their cysteine residues are superimposed, the six cysteines are found at positions 7, 14, 20, 21, 26 and 34. To make this alignment, gaps were introduced at the positions shown as dashes in the figure. In the analysis below, these gaps retain the assigned number shown in 2E, even though they represent amino acid deletions in the respective groups of active HG-1 peptides. By "active" is meant that the peptide compound is at most 1.5 log unit (about 30 times) and preferably, at most 1 log unit (10 times) less potent in blocking a class E voltage-gated calcium channel than is HG-1.

Using the aligned sequences as a guide, HG-1 peptide analogs or derivatives can be formed, using the following constraints:

1. The peptide includes Cys residues corresponding to positions 7, 14, 20, 21, 26 and 34, as illustrated with respect to HG-1, HG-2 and HG-3 in FIG. 2E.
2. The peptide is acidic at neutral pH and is generally hydrophobic in character.

Constraints 1 and 2 preserve the basic conformation of the class E voltage-gated calcium channel blocking peptides imposed by the physicochemical characteristics and the disulfide bridging pattern that are characteristic of this class of compounds. In conjunction with these rules 1 and 2, conservative derivatives of the exemplified peptides shown in FIGS. 2A-2D are formed, taking into consideration rules 3 and 4 below, and the more general HG peptides are formed taking into consideration the above rules 1 and 2 in conjunction with rules 3 and 5 below.

3. Amino acid positions that are identical among peptides HG-1, HG-2 and HG-3 (FIG. 2E) or that are identical among peptides HG-1, R9, R11, HG-8 and SNX-629 (FIG. 2F) are conserved. Thus, for example, in addition to the Cys residues described above, for the HG-1/HG-2/HG-3 composite peptide, the amino acids corresponding to at positions 1–9 (SEQ ID NO: 16) are conserved.

Further, with reference to the HG-1/HG-2/HG-3 composite peptide, in forming conservative HG-1 peptide derivatives, amino acid variations which occur at the eleven non-conserved residues (positions 10, 15–17, 27–32, and 38) are allowed to vary between the amino acid substitutions present in the parent peptides HG-1, HG-2 and HG-3. That is, assigning to the above-listed conserved positions the indicia $X_1$–$X_{11}$, this group of compounds includes peptide structures having the form: SEQ ID NO: 16-$X_1$-FGGC-$X_2X_3X_4$-SEQ ID NO: 17-$X_5X_6X_7X_8X_9X_{10}$-SEQ ID NO: 18-$X_{11}$-TFSD, where $X_1$=M or L; $X_2$=S or T; $X_3$=V, K or R; $X_4$=N or D; $X_5$=K, Q, or a deletion; $X_6$=H, R, or L; $X_7$=S or K; $X_8$=L or G; $X_9$=F or Y; $X_{10}$=S or N; and $X_{11}$=L, F, or G; as indicated in FIG. 2E.

Further derivatives are formed taking into consideration substitutions available based on standard substitution classes (i.e., the six classes based on common side chain properties and highest frequency of substitution in homologous proteins in nature, as determined, for example, by a standard Dayhoff frequency exchange matrix (Dayhoff)). These classes are Class I: Cys; Class II: Ser. Thr, Pro, 4Hyp, Ala, and Gly, representing small aliphatic side chains and OH-group side chains; Class III: Asn, Asp, Glu, and Gln, representing neutral and negatively charged side chains capable of forming hydrogen bonds; Class IV: His, Arg, and Lys, representing basic polar side chains; Class V: Ile, Val, and Leu, representing branched aliphatic side chains, and Met; and Class VI: Phe, Tyr, and Trp, representing aromatic side chains. In addition, each group may include related amino acid analogs, such as ornithine, homoarginine, N-methyl lysine, dimethyl lysine, or trimethyl-lysine in class IV, and cyclohexylalanine or a halogenated tyrosine in Group VI. Further, the classes may include both L and D stereoisomers, although L-amino acids are preferred for substitutions. Based on the above-cited classes, substitutions at the variable positions in the sequence SEQ ID NO: 16-$X_1$-FGGC-$X_2X_3X_4$-SEQ ID NO: 17-$X_5X_6X_7X_8X_9X_{10}$-SEQ ID NO: 18-$X_{11}$-TFSD above may be selected from within the following classes: $X_1$=Class V; $X_2$=Class II; $X_3$=Class IV or V; $X_4$=Class III; $X_5$=Class III or Class IV or deletion; $X_6$=Class IV or V; $X_7$=Class II or IV; $X_8$=Class II or V; $X_9$=Class VI; $X_{10}$=Class II or III; and $X_{11}$=Class II, V or VI.

By way of further example, and also forming part of the present invention, FIG. 2F shows alignment of selected sequences HG-1, R9, R11, HG-8, and SNX-629. These sequences may be combined, as discussed above, to form a composite sequence having the form: $V_1$-SEQ ID NO: 19-$X_2X_3X_4$-SEQ ID NO: 20-$X_5$-LGC-$X_6X_7X_8X_9X_{10}$-YCAW-$X_{12}X_{13}X_{14}X_{15}$ where $V_1$ is GVDKX$_1$G (SEQ ID NO: 51) or deletion, $X_1$ being A or P; $X_2$ is S or E, $X_3$ is V or K, $X_4$ is D or N, $X_5$ is R or K, $X_6$ is H or K, $X_7$ is S or D, $X_8$ is I or L, $X_9$ is F or L, $X_{10}$ is Y or deletion, $X_{11}$ is D or E, $X_{12}$ is L or V, $X_{13}$ is F or G, $X_{14}$ is S or E or deletion, and $X_{15}$ is F or D. This sequence can be further generalized to include at positions $X_1$–$X_{15}$ the Dayhoff class substitutions discussed above.

In a more general sense it is further appreciated that class E blocking peptides may be formed by making amino acid substitutions from the appropriate substitution classes referred to above. Moreover, it is appreciated that C- and/or N-terminal extensions of the peptide may be acceptable, so long as the aforementioned spatial relationship between the cysteine residues remains intact. The above amino acid substitution rules are intended as a guide for allowed amino acid substitutions within Class E voltage-sensitive calcium channel blocking peptides. Once an amino acid substitution or modification is made, the peptide is further screened for its ability to selectively block class E calcium channels, as described in Section II, The compound-test methods discussed in Section II can be used, also in accordance with the present invention, to identify calcium channel antagonist compounds which have class E channel blocking activity. In the screening method the test peptide is screened for its ability to selectively inhibit class E calcium channels. The test compound is selected for use in blocking class E channels in accordance with the present invention if the compound: (i) is effective to block calcium conductance by class E voltage-gated calcium channels at a concentration that is no more than about 10–50 times the concentration of HG-1 required to block such channels to an equivalent degree, and (ii) is unable to block by at least 50% L-type, T-type, P/Q-type or N-type calcium channels at molar concentrations that are about 10-times the molar concentration required to half maximally block class E voltage-gated calcium channels.

Preferred screening methods are described in Section II, below, and are detailed in Examples 5–9.

II. Pharmacological Profile of Class E Voltage-gated Calcium Channels

This section describes the pharmacological properties of class E voltage-gated calcium channel blocking peptides. This pharmacological profile provides guidance for selecting peptides in accordance with the present invention, and more particularly, for selecting peptides for use in the treatment indications discussed in Section III, below.

In Section I, HG peptides and HG-1 derivative peptides have been defined as conforming to certain structural criteria. In addition, the present invention recognizes that useful peptides are selective in their ability to block class E voltage-gated calcium channels, as constructed in recombinant cells or isolated from natural sources, as discussed below.

A. Blockade of Class E Voltaqe-gated Calcium Channels

Class E calcium currents may be measured in any of a number of ways known in the art to assess calcium movement across excitable membranes, such as by depolarization-induced calcium influx into cells, or whole cell or terminal patch clamp (electrophysiological techniques, See Example 6). In general, class E antagonist HG peptides antagonize these currents, preferably at a molar concentration that is at most 10–50 times higher than the molar concentration at which HG-1 exhibits its effects on other currents.

In order to determine whether: a particular test compound is selective for class E channels, calcium channel activity can be measured in several cell types, each selected for its relative uniformity of voltage-sensitive ion channels: The anterior pituitary cell line, GH3, has both L-type and T-type calcium currents; the IMR-32 neuroblastoma cell line is reported to contain a significant proportion of N-type calcium channels (Carbone et al. 1990); the 192C cell line was stably transfected to express the class E channel, as discussed herein; further, a neurohypophysial terminal preparation from the posterior pituitary expresses a previously "drug-resistant" calcium current, which, in accordance with experiments carried out in support of the present invention, is now thought to be a class E channel. In addition, sodium and potassium channel activity was measured in IMR-32 cells, and selected channels (class A calcium and potassium channels) were transiently expressed in Xenopus oocytes for additional channel, activity measurements, as discussed below.

1. Electrophysiolocical Measurements.

Calcium channel activity is conventionally measured using whole cell patch clamp recording of calcium currents.

One or more preparations shown to have class E channels may be used for this purpose. In one preparation, the neurohypophysial terminal preparation, detailed in Example 6B and discussed below, a pharmacological cocktail is employed to block other types of calcium channels (e.g., P/Q-type and L-type channels) as well as sodium channels present in the preparation. The residual high voltage-activated current is sensitive to HG-1 and is therefore defined as a class E channel. This preparation is amenable to standard, patch-clamp methods, as described in Example 6B.

Figure 5:
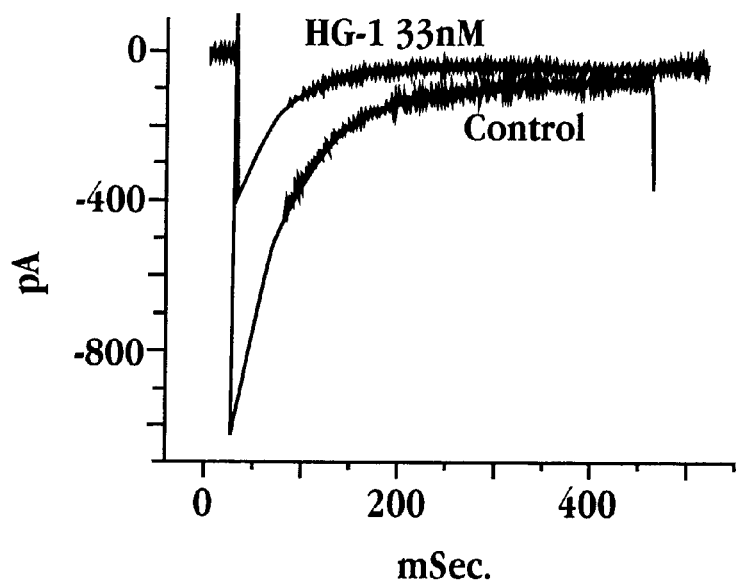

Alternatively, mammalian cells can be made to stably co-express a class E channel by adding to the cell coding sequences for the various subunits of this channel. As an example, the human alpha 1E (WO 95/04144), rat $\alpha_2$ (U.S. Pat. No. 5,407,820) and $\beta$ calcium channel subunits can form within a class E channel, when coding sequences for these subunits are co-transfected into cells. Alternatively, the human alpha 1E subunit can be combined with $\alpha_2$ and $\beta$ subunits from other sources to form an electrophysiologically functional channel for testing, according to methods known in the art.

a. Whole cell experiments. FIG. 5 shows a waveform of the calcium current measured in the presence and absence of 33 nM HG-1 in by whole cell patch clamp of a 192C cell (HEK cell stably transfected with alpha-1E subunit (Horne, et al. 1995). The current was elicited by a pulse to 0 mV from a holding potential of −90 mV, according to the methods described in Example 6A. Analysis of the decay of current showed a single exponential decay of the calcium current evoked in the 192C cells (rate constant=12.5 sec-1) in the presence or absence of 33 nM HG-1 (kinetic analysis after subtraction of the presumed steady state current values measured at 400 mSec.).

Figure 6:
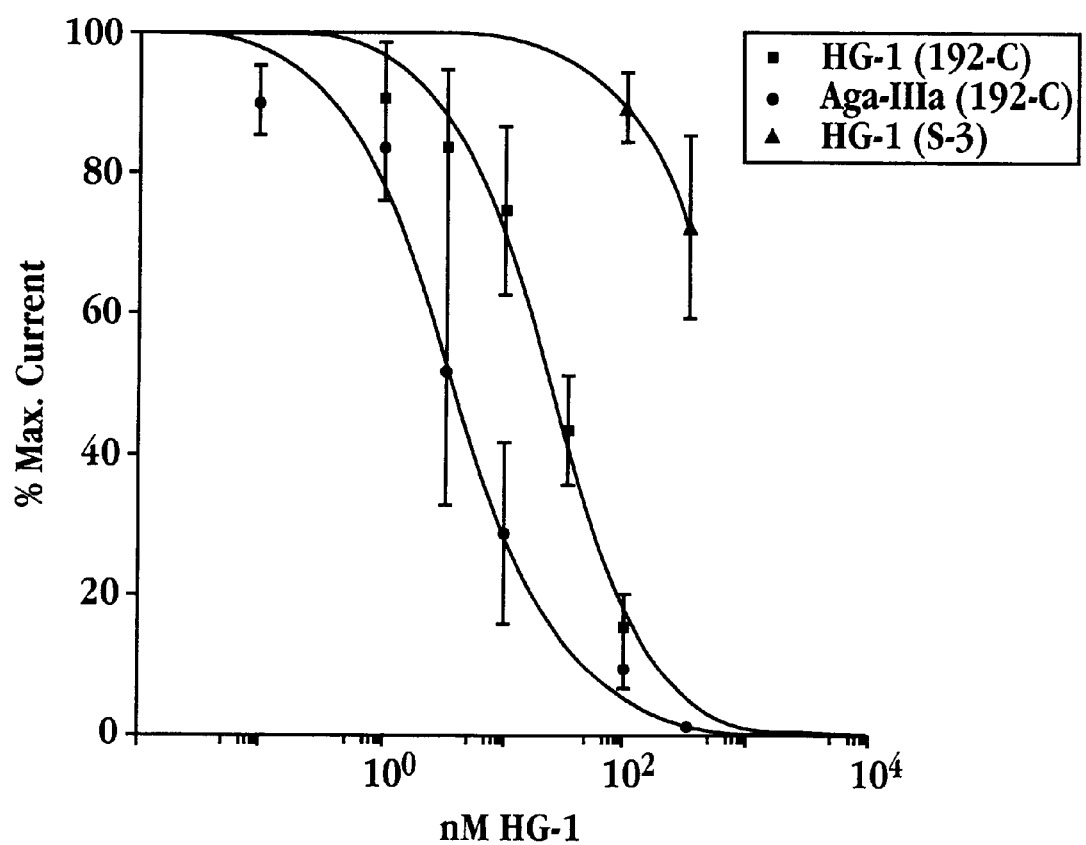

To determine concentration-effect parameters, recordings were obtained at different concentrations of HG-1, where peptide effects were evaluated at the peak of the inward current, as determined above. FIG. 6 shows the effects of varying concentrations of HG-1 and Aga IIIA on the peak inward calcium current in 192C cells. Also shown in FIG. 6 is the effect of varying concentrations of HG-1 on S-3 cells stably expressing class B type alpha-1 subunits (S-3), where each data point represents the mean and standard deviation from 3–5 independent measurements at each concentration, with one cell being used at 1 or 2 concentrations.

As shown, HG-1 blocks the class E current expressed in 192C cells with an $IC_{50}$ of 25 nM, while that for the class B current is estimated to be about 800 nM. Both of these values agree well with the apparent $IC_{50}$ values obtained in the depolarization evoked channel experiments using INDO-1, as discussed below. Aga-IIIA blocked the class E calcium current in the 192C cells with an $IC_{50}$ of 4 nM. This value is also consistent with the results of the INDO-1 experiments described below.

Selectivity of HG-1 for Class E currents was further demonstrated in a Xenopus oocyte system, wherein the oocytes were made to express class A alpha-1 subunits. Aga IIIA and cadmium on measured for effects on P/Q calcium channels. In these experiments, barium currents (4 mM barium, no added calcium, in medium) through the calcium channels were measured for technical reasons, in accordance with methods known in the art. At a concentration as high as 280 nM, HG-1 had no effect on the current. In contrast, 60 nM Aga-IIIA partially blocked and cadmium completely blocked this current.

b. Neurohypophysis terminal experiments. In additional experiments carried out in support of the present invention, it has been found that class E blocking HG peptides block a population of voltage-gated calcium channels present in neuroendocrine tissue that were previously found to be resistant to cocktails of other known calcium channel blockers. Example 6B provides details of the preparation of and electrophysiological testing of compounds in neurohypophysial terminals. These terminals have been recently shown to release certain peptide hormones (oxytocin, vasopressin) in a manner that is differentially regulated by the various calcium channels identified in the neurons (Wang). Thus, studies attempting to correlate electrophysiological parameters and peptide release have revealed that vasopressin (AVP) release can be inhibited in a manner that is consistent with regulation by a combination of L-type, N-type and P/Q-type calcium channels; in contrast, in the presence of pharmacological blockers of the foregoing channel types, a residual, stimulated oxytocin release still persists (WANG).

Figure 7:
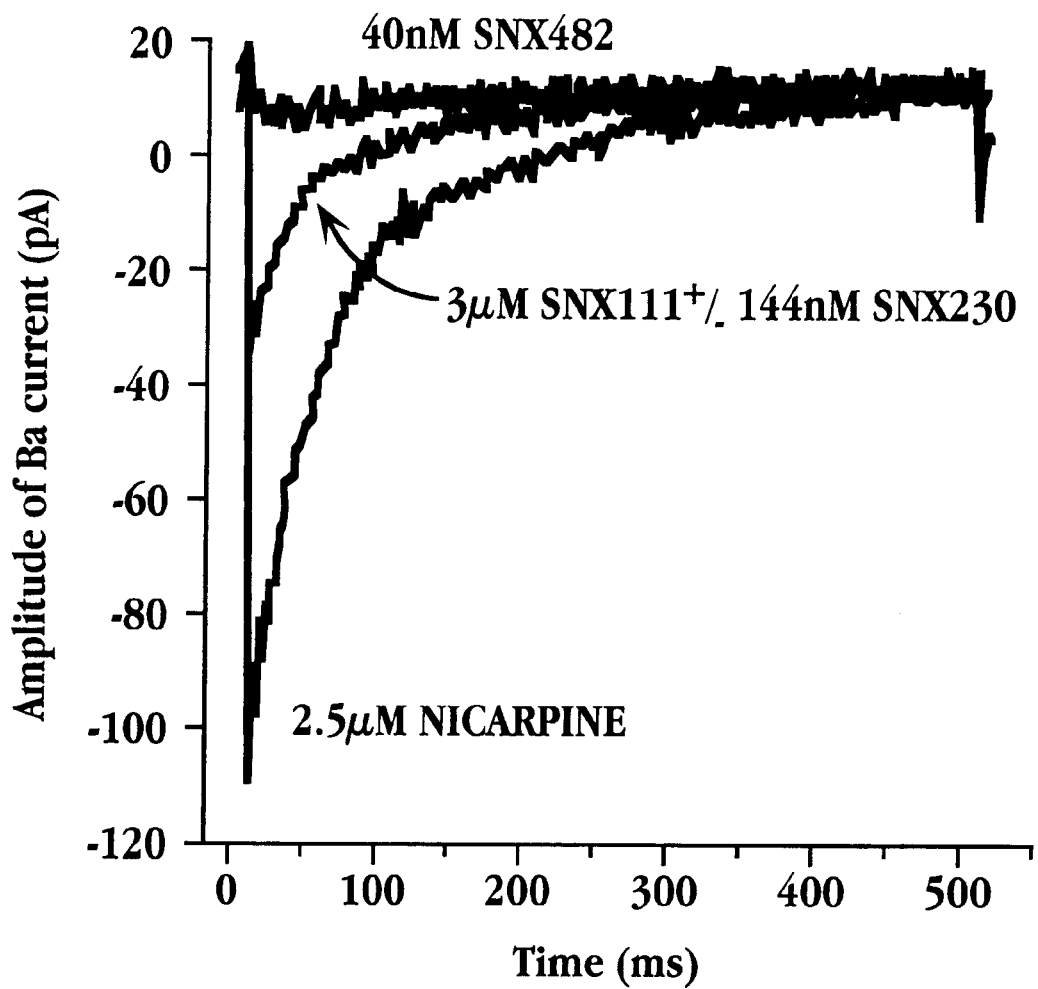

In the same neurohypophysis terminal preparation, as shown in FIG. 7, nicardipine was used to block L-type currents in nerve endings at a concentration of 2.5 $\mu$M. Addition of a combination of high concentrations of the N- and P/Q-type blockers SNX-111 (3 $\mu$M) and SNX-230, (144 nM) blocked part but not all of the remaining current. Further, addition of HG-1 peptide (SNX-482) at a concentration of 40 nM resulted incomplete blockade of the residual current.

Similar methods can be used to test potency of additional class E blocking peptide candidates, in accordance with the present invention.

2. Depolarization-evoked Calcium Influx.

Voltage-sensitive calcium channel activity can also be measured in excitable cells by measuring the influx of calcium in response to a depolarizing event, such as electrical stimulation, a stimulatory neurotransmitter, or a high concentration of extracellular potassium. Thus, a compounds ability to block depolarization-stimulated calcium influx is an indicator of its channel blocking activity.

This technique is particularly effective for determining channel specificity, when the preparations used have a single channel type or predominantly a single channel type. In some cases, as discussed below, influx of ions through a secondary channel can be blocked with a known antagonist of that channel, so that measurement is through the primary channel of interest. To monitor N-type calcium channel activity in IMR-32 cells, a saturating concentration of nitrendipine (a dihydropyridine) was also added to block L-type, calcium channels in the cells. Likewise, GH-3 cells were exposed to a saturating concentration of nitrendipine to measure only T-type calcium channel activity.

Detailed methods for measuring calcium currents in the three cell lines are described in Example 5. Briefly, cells are loaded with the calcium indicator dye INDO-1 acetoxymethyl ester (Molecular Probes), according to conventional methods. Test compounds are added to the cells, in the presence of any secondary channel blocker, as discussed above. The cells are then exposed to a depolarizing concentration of potassium ion. Influx of calcium is measured by change in fluorescence of the INDO-1 dye present in the cells. Upon stimulation with potassium, intracellular calcium in the cells typically increases from a baseline of 100–150 nM to a stimulated values of close to 1 $\mu$M. Concentration effect curves can be calculated from these data, as described in Example 5.

Independent experiments with calcium antagonists specific for L-type currents (nitrendipine), N-type currents (SNX-111=synthetic omega-conopeptide MVIIA), as well as with less selective calcium antagonists (SNX-230= synthetic omega-conopeptide MVIIC, and omega-Aga-IIIA and felodipine) were used to verify the pharmacological specificity of the different assay signals.

Fluorescence studies are carried out on whole cells that are genetically engineered to express the calcium channel alpha 1E subunit, such as the 192C cells described above; alternatively, such studies can be carried out on neurohypophysial terminal preparations, according to methods known in the art. The depolarization evoked increase in internal calcium in the genetically altered cells is resistant to omega conopeptides MVIIC and MVIIA, which block P/Q channels and N-type calcium channels, respectively, and the dihydropyridine (L-channel blocker) nitrendipine. In such experiments, the time course of the evoked change in ratio of INDO-1 fluorescence at 400 nm to that at 490 nm is related to calcium concentration as described by Grynkiewicz et al. (1985).

Figure 8A:
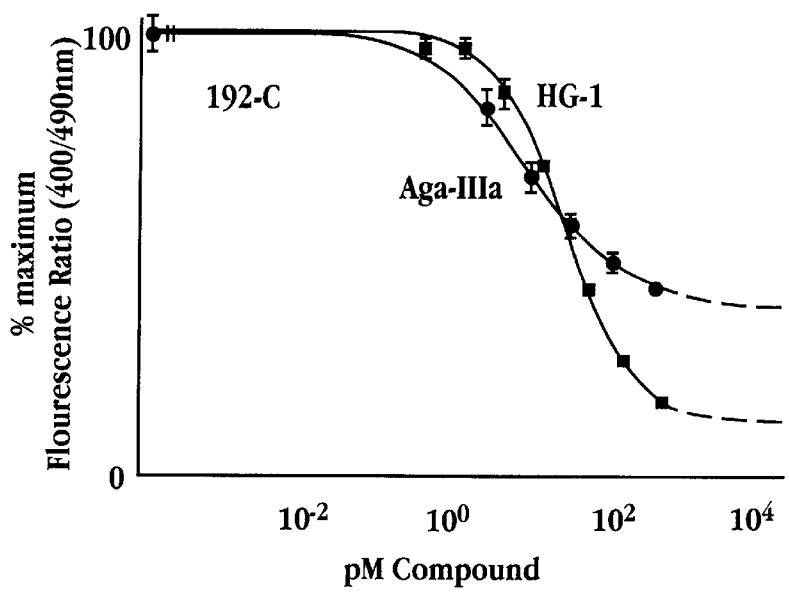

FIG. 8A shows concentration effect curves from the type of INDO experiments described above. The data are expressed as percent fluorescence ratio, which provides an estimate of calcium present in the cells under control conditions (e.g., percent calcium content of cells stimulated by potassium in absence of channel blocker). As shown, HG-1 blocked potassium-stimulated calcium influx into these cells with an apparent $IC_{50}$ of 15 nM (FIG. 8A, solid squares).

Aga-IIIA also blocks depolarization-evoked calcium influx into the cells (apparent $IC_{50}$ 5 nM, FIG. 8A, solid circles). These results are consistent with the pharmacology of the class E $Ca^{++}$ channels (Palma et al. 1994).

Figure 8B:
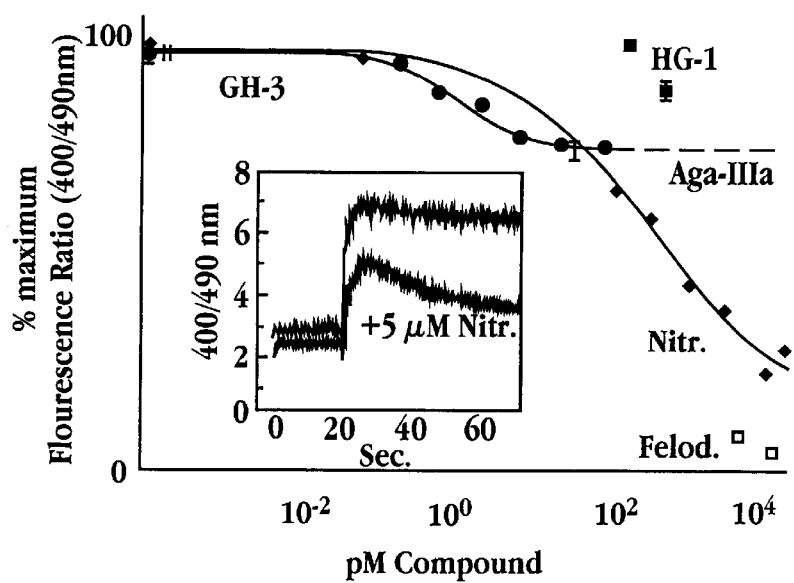

In contrast, HG-1 did not block calcium influx into GH-3 cells or IMR-32 cells, as discussed below. The anterior pituitary cell line, GH3, is reported to exhibit both L-type and T-type calcium currents by whole cell patch clamp recording of barium currents (Lievano et al., 1994). Consistent with this, the dihydropyridine nitrendipine blocked only a sustained component of the depolarization evoked increase in internal calcium which did not inactivate over 60 seconds (apparent $IC_{50}$ 400 nM), and, even at concentrations over 5 $\mu$M, did not completely block transient increases in internal calcium (FIG. 8B and inset). The remaining transient increase in internal calcium was completely blocked by the dihydropyridine felodipine (apparent $IC_{50}$ 600 nM). This dihydropyridine completely blocks the T-type calcium channel in myocardial cells at concentrations of 4 $\mu$M and below (Cohen et al., 1994). HG-1, at concentrations of 500–600 nM, had no effect on the total internal calcium increase evaluated at 40 seconds after depolarization, and also had no effect on the peak in internal calcium (at 10 seconds after depolarization) in the presence of 5 $\mu$M nitrendipine (FIG. 8B, inset), indicating that HG-1 does not inhibit either L-type or T-type currents. In contrast, Aga-IIIA produced a potent but partial block of the depolarization evoked signal in these cells (FIG. 8B, apparent $IC_{50}$=1.5 nM, evaluated at 60 seconds after depolarization), consistent with its reported potent block of the L-type current in myocytes (Cohen et al., 1994).

Figure 8C:
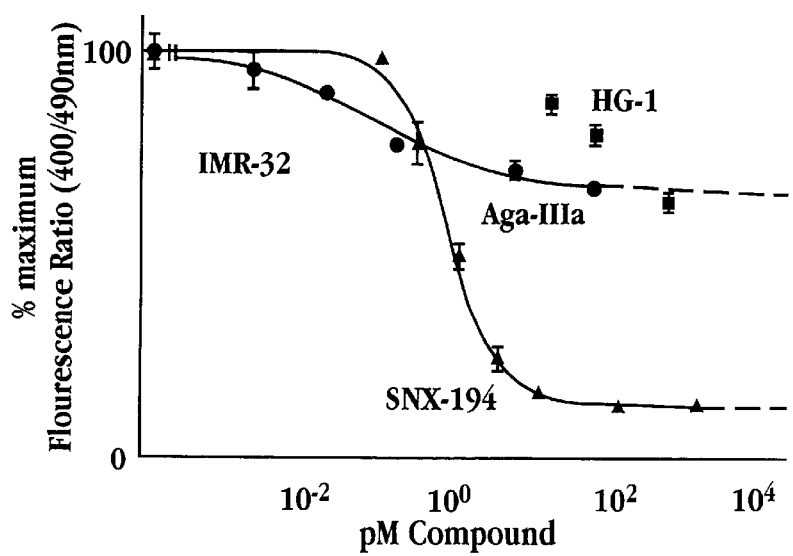

Also as discussed above, the IMR-32 neuroblastoma cell line has a calcium (barium) current which is sensitive to the N-channel selective omega-conopeptide GVIA (Carbone et al. 1990). Consistent with this observation, in a preparation of these cells that included nitrendipine to block L-channel activity, SNX-194 (an N-channel blocking omega conopeptide that is the met-12 to nle-12 derivative of omega conopeptide MVIIA), nearly completely inhibited the remaining transient depolarization evoked increase in internal calcium, with an apparent $IC_{50}$ of 1 nM (FIG. 8C). Aga-IIIA had a similar effect on the evoked increase in internal calcium concentrations in IMR-32 cells (apparent $IC_{50}$=0.1 nM). HG-1 had a small effect on this current, but only at relatively high concentrations ($IC_{50}$>400 nM).

When perfused at 140 nM, HG-1 had no effect on sodium and potassium currents in IMR-32 neuroblastoma cells, measured according to the methods detailed in Example 7. HG-1 also had no effect on the individual cloned potassium channels Kv1.1, Kv1.2, and Kv1.4 in the Xenopus oocyte expression system, measured as detailed in Example 9.

B. Selectivity for Class E Calcium Channels

The studies discussed in Part A, above, also point out a second important feature of HG peptides—namely, their selectivity for blockade of class E calcium currents relative to other types of calcium currents. For example, although the spider peptide omega-Aga IIIA antagonizes the class E calcium channel (Palma et al. 1995), it is not considered a selective ligand because it also potently blocks N and L-type calcium currents (Cohen et al. 1993, Ertel et al. 1994). In contrast, as demonstrated by the studies described above, the exemplary HG peptide HG-1 has virtually no effect on N-type, L-type, P/Q-type, or T-type calcium currents, or on potassium or sodium channels, when tested on such channels at concentrations that are at least 10 times the concentrations at which it half maximally blocks class E voltage-gated calcium channels.

C. Selection of Class E Calcium Channel Antagonists

From the foregoing experiments carried out in support of the present invention, it can be seen that HG peptides (e.g., peptides exhibiting the structural features described in Section IB and the pharmacological features discussed in Section II), specifically block class E calcium channels, as evidenced by the relatively low concentrations at which the HG peptides block current through such channels ($IC_{50}$'s 15–25 nM) compared to the relatively high concentrations at which the compounds block current through other known classes of calcium channels (e.g., the N-type ($IC_{50}$ approx. 800 nM), P/Q-type, T-type and L-type calcium channels).

In accordance with the present invention, peptides that are selective for calcium channels will conform to both the structural constraints described in Section I, above and to the activity profile described above. Thus a class E channel-selective blocking peptide is one which conforms to the basic structural constraints described in Section I, above: it includes Cys residues at positions corresponding to positions 7, 14, 20, 21, 26 and 34 shown in FIG. 2E and preferably has three intrachain disulfide linkages. In one general embodiment, the HG peptide will conform to the general form of the composite of the HG-1/HG-2/HG-3 or of the HG-1/HG-8/R9/R11/SNX-629 peptides illustrated, but may include substitutions from within the Dayhoff substitution groups described for each of the additional positions in the chain. In another embodiment, class E calcium channel blocking HG peptides will retain the conserved regions described for one or more or the composite peptides described herein, and the variable regions will include substitutions from the classes defined by each of the variable positions. For example, in the case of the HG-1/HG-2/HG-3 peptide, the peptide will take the form: SEQ ID NO: 16-$X_1$-FGGC-$X_2X_3X_4$-SEQ ID NO: 17-$X_5X_6X_7X_8X_9X_{10}$-SEQ ID NO: 18-$X_{11}$-TFSD, where the variable positions $X_1$–$X_{11}$ are selected from the Dayhoff substitution classes as follows: $X_1$=Class V; $X_2$=Class II; $X_3$=Class IV or V; $X_4$=Class III; X=Class III or Class IV or deletion; $X_6$=Class IV or V; $X_7$=Class II or IV; $X_8$=Class II or V; $X_9$=Class VI; $X_{10}$=Class II or III; and $X_{11}$=Class II, V or VI.

In still another embodiment, amino acid variations which occur at the eleven non-conserved residues (positions 10, 15–17, 27–32, and 38) are allowed to vary between the amino acid substitutions present in the parent peptides. In this latter, more limited, sense, using the HG-1/HG-2/HG-3 peptide as an example, the peptide will take the form: SEQ ID NO: 16-$X_1$-FGGC-$X_2X_3X_4$-SEQ ID NO: 17-$X_5X_6X_7X_8X_9X_{10}$-SEQ ID NO: 18-$X_{11}$-TFSD, where $X_1$=M or L; $X_2$=S or T; $X_3$=V, K or R, $X_4$=N or D; $X_5$=K, Q or a deletion; $X_6$=H, R or L; $X_7$=S or K; $X_8$=L or G; $X_9$=F or Y; $X_{10}$=S or N; and $X_{11}$=L, F, or G; and as indicated in FIG. 2E. The foregoing substituted peptides are termed "HG-1/HG-2/HG-3 composite peptides" herein.

A peptide selected according to the above criteria is useful in the context of the present invention if it is selective for class E calcium channels. Part B of this Section describes a panel of assays that may be used to measure such selectivity. In particular, the compound is deemed selective for class E channels if it exhibits an ability to block class E channels at much lower concentrations than it blocks other known calcium channels (e.g., N-type, L-type, T-type and P/Q-type channels) or other ion channels that are important in electrically excitable cells (e.g., sodium or potassium channels). By "much lower concentrations" is meant that there is at least a 10–50-fold differential in the effective molar concentration (measured as $IC_{50}$, or more preferably $K_i$) for inhibition of the class E type calcium channel as opposed to inhibition of other ion channels, particularly L-type, N-type, and T-type voltage-gated calcium channels. Thus, using the peptide HG-1 (SEQ ID NO: 1) as an example: HG-1 conforms to the most conservative of the structural constraints defined in Section I, above (e.g., Rules 1–4). When tested for class E calcium channel selectivity, the peptide exhibited $IC_{50}$'s in the range of 15–25 nM in blocking class E channels, by two separate measures of channel blocking activity. HG-1 showed no evidence of blocking L-type, T-type or P/Q type channels, and blocked N-type channels with $IC_{50}$ in the range of >400–800 nM. The compound also showed no evidence of blocking either potassium or sodium channels at relatively high concentrations. Thus HG-1 shows selectivity for class E calcium channel blockade.

Likewise, in experiments carried out in support of the present invention, it was shown that truncated HG-1 peptide SNX-629 (SEQ ID NO: 15) inhibition of class E calcium channels at a concentration that is less than about 20 times the concentration exhibited by HG-1 in the same assay (inhibition of calcium uptake); accordingly, SNX-629 is a candidate for an HG-1 derivative peptide that is effective to block class E channels, in accordance with the present invention.

As a counter-example, the peptide Aga IIIA also shows activity as a class E-channel blocker, as evidenced by an $IC_{50}$ of 0.1 nM (electrophysiological measurement) to 15 nM (calcium influx) in blocking the channel. However, Aga IIIA would not fall within the structure defined for class E calcium channel blocking peptides, as discussed above and illustrated in FIGS. 5 and 6. Moreover, the peptide is not R-channel selective, since it also blocks N-type calcium channels with an $IC_{50}$ of about 0.1 nM.

III. Utility

HG peptides and HG peptide derivatives that are selective antagonists of class E calcium channels may be useful in treating a number of disorders of the nervous system, particularly those that involve abnormal transmission of signals through the brain midline regions (caudate-putamen, thalamus, hypothalamus, amygdala, cerebellum) and in the nuclei of the ventral midbrain and brainstem, including projections into the pituitary, particularly from the hypothalamus, as illustrated below. The entry of calcium through the class E calcium channel may also act as an intracellular messenger involved in the modulation of other ion channels and cellular proteins. Thus peptides may affect signalling at both the cellular and network level. Nervous disorders that could benefit from blockade of Class E channels may include, but are not necessarily limited to, ischemic and traumatic brain injury, epilepsy, acute and chronic pain, as well as psychiatric disorders. Two exemplary applications of the observations of the present invention are discussed below.

A. Anticonvulsant Activity

In experiments carried out in support of the present HG peptides were tested in an standard experimental animal seizure model, the DBA/2 audiogenic seizure model, which is used to evaluate compounds for anticonvulsive activity for potential use in epilepsy and other brain seizure disorders. Testing procedures in this model are detailed in Example 11. Briefly, a genetically seizure-prone strain of mice, DBA/22 mice (Jackson Laboratories, Bar Harbor, Me.), exhibit a reproducible pattern of seizure behaviors when exposed to a particular frequency and intensity of sound. Compounds with a wide variety of structures have been found to be active in this model, which is, also independent of temperature. This latter point is particularly important in the context of calcium channel blockers, which induce hypothermia, which is also anticonvulsant in many animals.

Figure 9A:
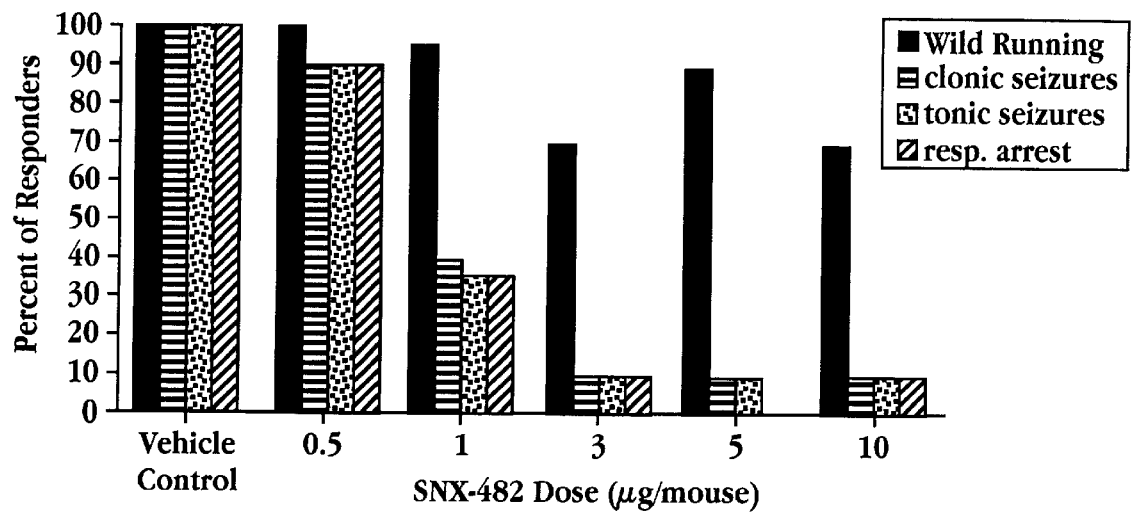
Figure 9B:
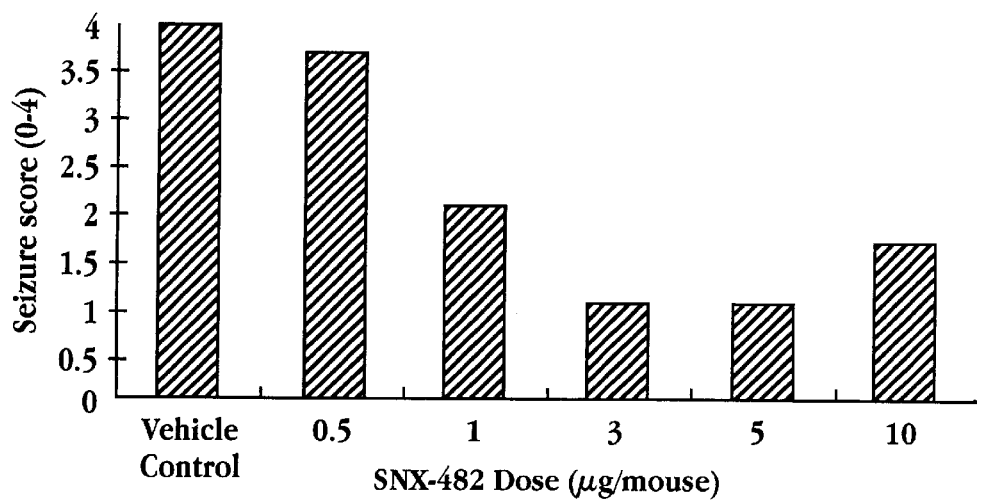
Figure 10:
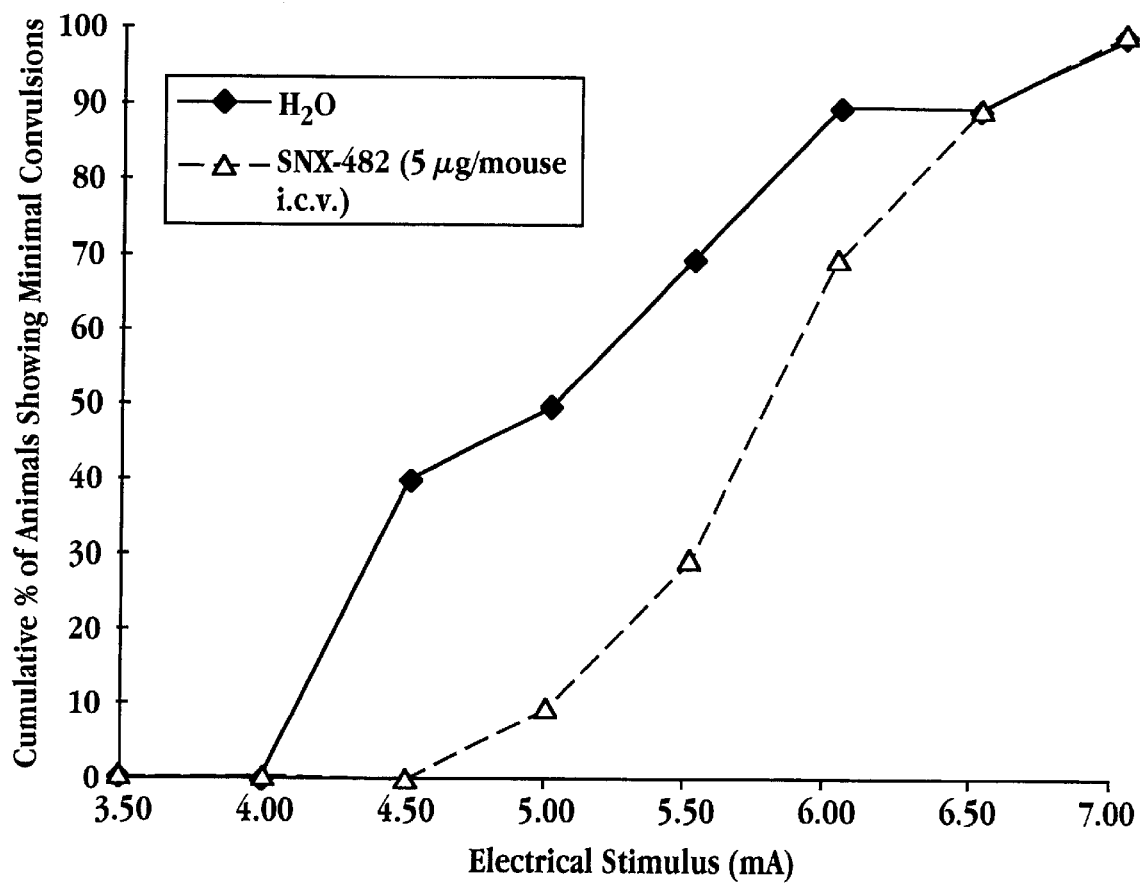
FIG. 10 shows cumulative dose-response curves of convulsions produced in response to an electrical stimulus in the absence and presence of HG-1 peptide SNX-482.

FIGS. 9A and 9B show the results of tests in which mice (18–21 days; approx. 7–10 g) were given doses ranging from 0.5 to 5 µg HG-1 (SNX-482) via an intracerebroventricular (i.c.v.) route 30 minutes prior to sound stimulus. In FIG. 9A is shown the percent of tested mice (N=10/dose) exhibiting each of the four predominant behaviors exhibited during the sound stimulus: wild running, clonic seizures, tonic seizures and respiratory arrest. FIG. 9B shows the overall seizure score for the various animals, where seizures were ranked in intensity on a scale of 0–4, 0=no seizure activity; 1, wild running only; 2, wild running+clonic seizures; 3, wild running, clonic seizures, and tonic seizures; 4, wild running, clonic seizures, tonic seizures, and respiratory arrest. The $ED_{50}$ for the anticonvulsant effect in the DBA/2 model is approximately 0.8 µg/mouse i.c.v. FIG. 10 shows cumulative dose-response curves for convulsions produced in mice in response to increasing electrical stimuli in the absence or presence of SNX-482.

Figure 11A:
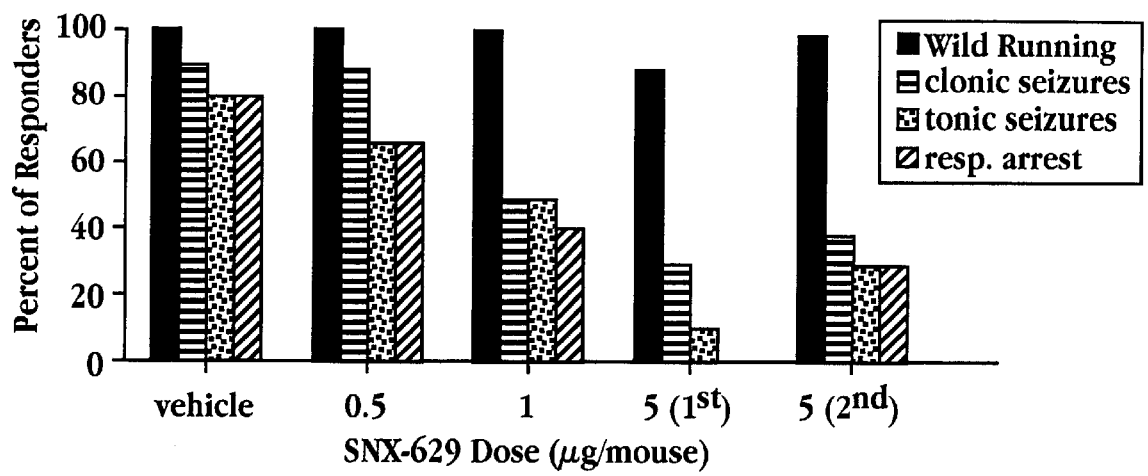
FIGS. 11A and 11B show the effects of varying does of SNX-629 on convulsive behaviors in DBA/2 mice subjected to audiogenic stimuli.
Figure 11B:
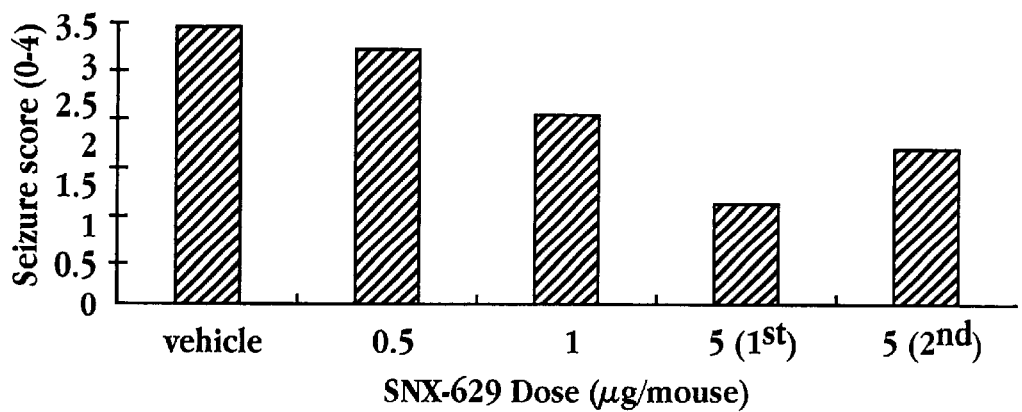
Figure 12:
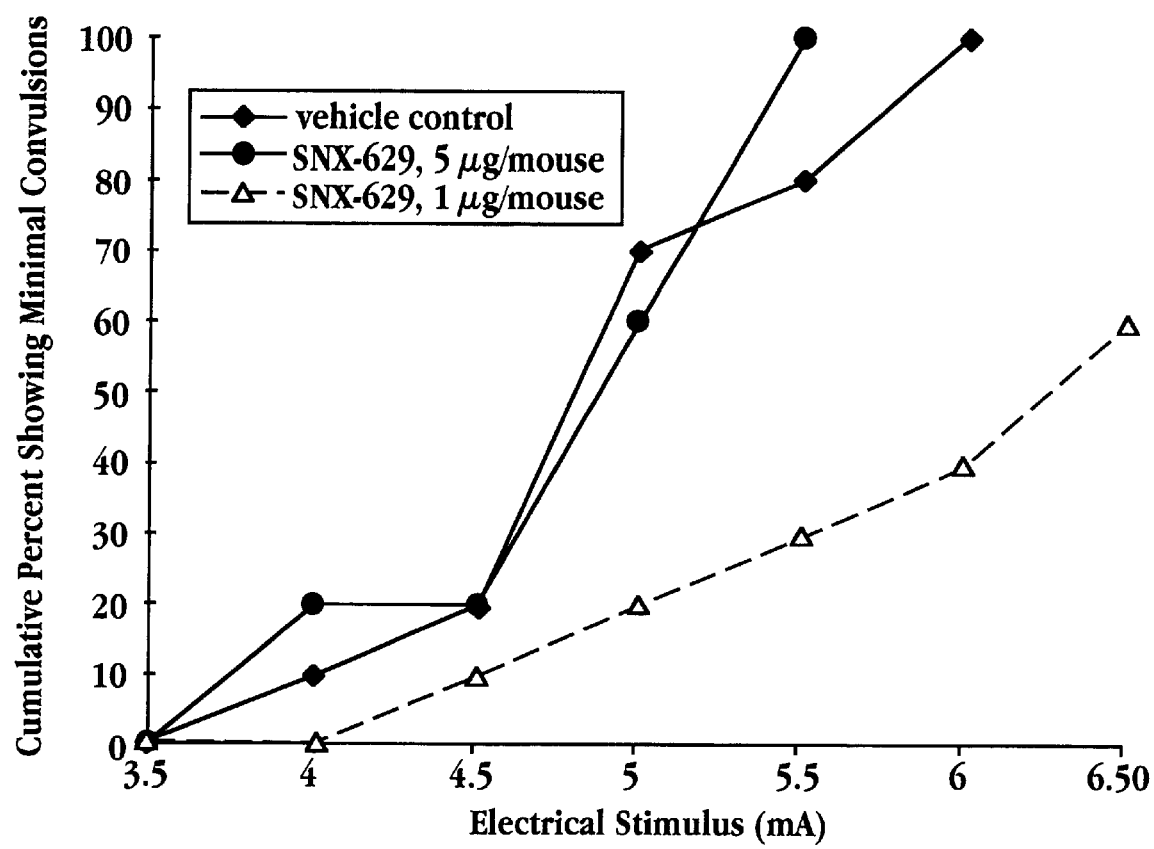
FIG. 12 shows cumulative dose-response curves for 0, 1 or 5 $\mu$g SNX-629 on electrically stimulated convulsions.

Likewise, FIGS. 11A and 11B show the results of studies in which DBA/2 mice were given SNX-629 i.c.v. prior to being exposed to the sound stimulus. Here an approximate $ED_{50}$ of about 5 µg/mouse was found. In the foregoing studies, values are generally derived from the graphs shown herein, and are based on 2–3 runs of 10 mice each. FIG. 12 shows the effect of treating mice with SNX-629 (1 or 5 µg) on electrically stimulated convulsions.

Based on the foregoing, it is apparent that HG peptides exhibit significant anticonvulsant activity.

B. Neuroendocrine Therapy

In experiments carried out in support of the present invention, and discussed above, it has been shown that R-type calcium channels are involved in oxytocin secretion. Oxytocin is involved in induction of labor in pregnant humans and in the milk let-down response in lactating mothers. HG-peptides can be used to inhibit oxytocin release from the pituitary for: (i) prevention of premature labor, and/or (ii) inhibition of the milk let-down response in cases where a lactating female either does not wish to nurse or wants to cease lactating.

For either of the foregoing methods, the peptide can be given by any route which effects a blood concentration sufficient to block calcium channels at the site of interest. For example, since the posterior pituitary is adjacent a rich capillary bed (the portal capillary plexus) into which it releases hormones, methods of administration which target the drug to this capillary bed are particularly advantageous for inhibiting oxytocin release from the neurohypophysis. Similarly, modes of administration which deliver the peptide to the brain are advantageous for providing anticonvulsant activity. Appropriate dosages can be extrapolated from the appropriate animal models, such as those described herein.

Exemplary modes of administration include, but are not limited to, intravenous administration, pulmonary delivery (nasal insufflation), use of a transdermal patch, and the like. Acceptable excipients suitable for peptide delivery by these methods are known in the art (Banga). Oral (gastric or preferably, buccal) as well as rectal delivery methods are also acceptable for peptides (Banga) and may be used in conjunction with the present invention.

Nasal administration of peptides has the advantage that it avoids the hepatic circulation in its first pass and therefore provides a relatively fast onset of a minimally diminished concentration of the peptide. The peptide can be formulated into a spray, in the presence of an appropriate salt and buffer to provide isotonicity and stable pH. While this method is generally most suitable for smaller peptides, use of certain penetration enhancers, such as lysophophatidyl choline or non-ionic detergents, may help effect transport of an HG peptide across the nasal mucosa.

Likewise, pulmonary administration avoids the hepatic first-pass effect. This mode of administration, as well as the precautionary measures that should be adhered to in utilizing it, are well known in the art. Generally, the peptide will be formulated into an aerosol preparation that is generated by a device, such as a metered-dose inhaler, a nebulizer or a dry powder inhaler. The aerosol is generated to have a selected mass median aerodynamic diameter (MMAD) that is a function of particle size, shape and density, for deposition in the pulmonary tract. Generally, particles having an MMAD of between about 1 and 6 $\mu$m are optimum for delivery to the lungs. Addition of permeation enhancers and/or protease inhibitors to the formulation may also be desirable.

While oral delivery of peptides through standard enteral (gastric) routes is possible; particularly in the case where the presumed site of action of the peptide is the pituitary, buccal or sublingual delivery of drug may be desirable. The buccal mucosa is that portion of the oral mucosa that covers the inside of the cheek. For peptides, the use of an oral mucosal adhesive dosage, form, such as a tablet with an adhesive surface (hydroxypropyl cellulose, carbopol), may facilitate drug absorption over prolonged contact. Penetration enhancers, such as non-ionic and ionic surfactants, in addition to peptidase inhibitors, may also facilitate absorption of peptides via this route. (Banga)

In selecting a method of administration, the clinician will be able to titrate the amount of inhibitor needed by the patient's response; for example, in treating premature labor, the clinician can monitor contractions and alter the amount of drug accordingly. For this use, intravenous delivery will be acceptable; however, any of the methods discussed above are also useful. Preferably, the amount of HG-peptide administered will be effective to produce a concentration of about 1–200 nM HG-1 peptide (or biologically equivalent amounts of related HG peptides); however, as mentioned above, the actual amount given will depend upon the clinician's assessment of patient response, in conjunction with other standard considerations related to patient's weight, circulatory status and the like. Such determinations are within the knowledge of persons skilled in the art.

Generally, in treating such nervous disorders, the compound will be effective if given in a dose that produces a concentration of about 10–100 nM or more at the site of action. Dosages and routes of administration required to produce such a concentration are routinely determined by persons skilled in the art, based on considerations such as the size of the subject to be treated, the site of action, and the pharmacokinetics of the compound.

The following examples illustrate, but in no way are intended to limit the present invention.

Materials and Methods

A. *Hysterocrates gigas* Venom

Venom from male specimens was collected by electrical field stimulation, and was flash frozen (Invertebrate Biologics, Los Gatos, Calif.).

B. *Agelenopsis aperta* Venom

Lyophilized venom was obtained from Spider Pharm (Feasterville, Pa.). The lyophilized venom (equivalent to 0.5 mL of initial venom volume) was applied directly to Sephadex G-50 (Pharmacia, Piscataway, N.J.) size exclusion columns after suspension in 0.5 mL of 0.1 N HCl.

C. Cell Lines

The human neuroblastoma cell line IMR-32, the rat pituitary line GH-3, and the humane embryonic kidney cell line 293 (HEK) were obtained from the American Type Culture Collection (ATCC Accession No. CRL1573; Rockville, Md.) and were maintained in RPMI 1640 medium (Gibco-BRL) supplemented with 2 mM glutamine and 10% fetal bovine serum. S3 and 192C cells are HEK cells that stably express the class B and class E calcium channels, respectively, as described below.

D. Transfection of HEK 293 Cells

A vector carrying the coding region for the human alpha-1E (h$\alpha$-1E) calcium channel subunit, was constructed in pcDNAIII as described in PCT publication WO 95/04144, both which is incorporated herein by reference. HEK cells were transfected by standard methods well known in the art (calcium phosphate or lipofectamine mediated transfection) to form 192C cells that expressed the class E voltage-sensitive calcium channel.

Similarly, S3 cells were formed by transfecting HEK cells with the human alpha-1B calcium channel subunit, as described by Ellinor et al. (1994).

E. Cell Culture Methods

S3 and 192C cells were maintained in DMEM supplemented with 10% fetal bovine serum (FBS), 0.4 mg/ml hygromycin B and 0.6 mg/mL geneticin G418 (both from Boeringer Mannheim, Indianapolis, Ind.), and were used 2 days after plating onto glass coverslips.

For electrophysiological studies, IMR-32 cells were grown in Dulbecco's minimal essential medium (DMEM, Gibco-BRL) supplemented with 10% FBS, and were used without differentiation. For the assay of internal calcium concentrations, the cells were grown in Eagle's minimal essential medium with Earle's salts, supplemented with 10% FBS, 2 mM glutamine and an antibiotic/antimitotic mixture (Gibco-BRL). These cells were differentiated by the addition of 1 mM dibutyryl CAMP and 2.5 uM bromodeoxyuridine (both from Sigma, St. Louis, Mo.) and were used 7–15 days after differentiation.

GH-3 cells were cultured in Hams F-10 medium with 15% horse serum, 2.5% FBS and antibiotic/antimitotic mixture.

EXAMPLE 1

Purification of HG-1

The isolation of HG-1, from *Hysterocrates gigas* was performed on a Gilson HPLC using the general methods described in Newcomb et al. (1989). The venom (20 to 150 µL) was thawed and immediately thereafter was applied to a 4.5×250 mm "wide pore" octadecylsilica column (Vydac) packed with 5 µm particles. Elution was monitored by absorbance at 220 nm with a Gilson Holochrome detector, as well as by endogenous fluorescence with a Hewlett-Packard Model 1046A fluorescence detector (excitation 260 nm, emission 340 nm 280 nm emission cutoff filter). Elution was with a linear gradient of methanol in 12 mM sodium phosphate (pH 6.2) of 0–100% over 125 min. at 1 mL/min. (Prior to reuse, the column was washed with a gradient from 0.1% TFA to methanol, in order to remove components which did not elute with the pH 6.2 buffer). Components that antagonized the class E calcium channel were localized in the 1 mL fractions by the patch clamp electrophysiological method described in Example 8, below, and methanol was removed from the active fraction (containing HG-1) in a vacuum centrifuge. Further fractionation used a linear gradient of 0–25% methanol in 0.1% trifluoroacetic acid (TFA) over 5 minutes, followed by a gradient of 25–80% methanol over 50 minutes.

Edman degradation, as well as amino acid analysis of those amino acids not present in HG-1 (glu and ile), showed the TFA purified material to be 95–99% pure (with the early eluting part of the peak being of greater purity). For confirmation of the activity of HG-1, the active material from this separation was rechromatographed using an aqueous buffer of 0.05% heptafluorobutyric acid (HFBA) (0–65% methanol over 5 minutes, followed by 65–85% over 50 minutes). This material was of 99% or greater purity, as assessed by Edman degradation and amino acid analysis.

EXAMPLE 2

Purification of Omega-Aga-IIIA

Omega-Aga-IIIA (Venema et al. 1992) was isolated by size exclusion chromatography of *A. aperta* venom on Sephadex G-50, followed by two steps of reversed phase chromatography (with the same Vydac column as described in Example 1); the first using a gradient of from 20 mM potassium phosphate pH 2.8 to acetonitrile, and the second using a gradient of from 0.1% TFA to acetonitrile (both radients at 0.75% acetonitrile per minute). Characterized omega-Aga-IIIA was kindly provided by Dr. Mike Adams (University of California, Riverside), and was used as a standard to monitor the elution position of the peptide. Edman degradation of the native peptide through 20–30 cycles was used to verify that fractions contained predominantly the Aga-IIIA sequence (typically >95%), and mass spectral analysis with the electrospray method was used to show that the samples consisted of Aga-IIIA (as opposed to the variants described by Ertel et al. 1993). If this was not the case, the Aga-IIIA was further purified using a gradient of from 0.0 5% HFBA to methanol (1.6750 methanol per minute), resulting in a preparation of the peptide of 99% or greater purity.

EXAMPLE 3

Structural and Sequence Determinations
A. Amino Acid Analysis

Purified peptide samples were subjected to acid hydrolysis or enzymatic degradation prior to amino acid analysis. Acid hydrolysis was carried out on samples (50–70 pmol of purified HG-1 per vial) in 6 N HCl in TEFLON stoppered autosampler vials at 110° C. for 20 and 48 hours. Amino acid content of acid hydrolysates was determined by comparison to standards (100 pmol of each L amino acid) that had also undergone the hydrolysis procedure.

Compositional and C-terminal analyses were performed by reversed phase chromatography and fluorometric detection following derivatization of acid or enzymatic hydrolysates with N-acetyl-L-cysteine and o-phthaldialde-hyde (OPA) (Bruckner et al. 1989). Diluted hydrolysates were placed in autosampler vials in 40 µL of dimethylformamide-:water 1:9, and a Gilson 231–401 autosampler was programmed to add 25 µL of 1 mg/mL of the OPA followed by 50 µL of 1 mg/mL of the thiol, both in 0.5M potassium borate, pH 10. Following mixing (approx. 1 min.), the derivatives were injected onto a 4.5×250 mm Phenomonex Primesphere "HC" octadecylsilica column (5 µM particles; Torrance, Calif.) equilibrated with 15 mM sodium phosphate pH 6.2 and eluted with a gradient to 65% methanol over 87 minutes. Detection was with the Hewlett-Packard 1046A fluorescence detector set to excitation at 340 nm and emission at 408 nm (408 nm emission cutoff filter). This system resolved the D and L enantiomers of all of the primary protein amino acids, with the exception of histidine (proline and cysteine are not detected).

The ratios of the amino acids were determined by comparison to L-amino acid standards which had been subjected to identical hydrolysis procedures (20 or 48 hr at 110° C. in 6 N HCl). Chirality was determined by comparison to L and DL standards, and racemization was less than 5% in the 20 hour hydrolysates. The analysis shown in Table 1 represents 10 independent hydrolysates of 50–70 pmol of both the TFA (two system) and HFBA (three system) purified material. Amino acids not listed (glu and ile) were present at 0.05 or less in the composition.

The chirality of Met and Trp was from analysis of carboxypeptidase digests of the native and,alkylated peptide. The quantitation of tryptophan is based on the ratio to threonine reached in carboxypeptidase Y digests of native HG-1.

B. Enzymatic Digestion of Peptide

Both native and alkylated HG-1 (250–500 pmol) were dried and digested with 0.3 µg of Carboxypeptidase Y (Pierce, Rockford, Ill.) in 100 µL of 0.1 M sodium phosphate pH 6.2. Aliquots (10 µL) were removed at various times, and amino acid analysis was used to confirm the presence of a single tryptophan residue in HG-1, as well as to confirm that the amino acids present were the L-enantiomers. Since the Carboxypeptidase Y digest did not give clear sequence information at the carboxyl terminus of HG-1, the digest of native HG-1 was repeated with agarose bound Carboxypeptidase A (Sigma), using the same digestion conditions as with the Carboxypeptidase Y.

In order to confirm the results of Edman degradation on the enzymatically treated samples, 1–2 nmol of HG-1 was dried and digested with 1 µg Trypsin (Pierce or Worthington, Freehold, N.J.) in 50 µl 0.1 M potassium phosphate pH 7.4 (4 hr. at 37° C.). Fragments were resolved as above, using a gradient of 0–100% methanol in 0.1% TFA over 1 hour.

C. Peptide Reduction and Alkylation

HG-1 (2 or 4 nmol of the TFA-purified material) was dried and derivatized with 4-vinylpyridine according to methods well known in the art (see, e.g., Tarr et al., 1983, Hawke and Yuan 1987).

D. Edman Degradation

Edman degradation was performed on the alkylated intact or digested peptides with an Applied Biosystems Model 477A Sequenator with a model 120A Analysis System (Perkin-Elmer, Foster City, Calif.) using procedures recommended by the manufacturer for chemistry and identification.

E. Mass Spectral Analysis of Petptides

Positive ion electrospray ionization-mass spectrometry (ESI-MS) analysis were, performed with a Finnigan MAT 900Q forward geometry hybrid mass spectrometer. Mass spectra were acquired at full accelerating potential (5 kV) and a scan rate of 10 s decade$^{-1}$. The electrospray ionization interface used is based on a heated glass capillary inlet. Sample solutions were prepared in 80:15:5 acetonitrile/water/acetic acid (v/v/v) and infused through the ESI source at a flow rate of 1 μL min$^{-1}$. The analysis used 1 nmol of TFA-purified HG-1.

Matrix-assisted laser desorption/ionization (MALDI) mass spectra were acquired on a PerSeptive Vestec Laser Tec Research time-of-flight mass spectrometer operating in the linear mode. Radiation from a nitrogen laser (337 nm) was used in the desorption process. Samples were prepared in a standard fashion by placing 1 μL of a aqueous solution of HG-1 (1–10 pmol/μL in 0.1% TFA) and 1 μL of the appropriate matrix solution [c. 5 mg/mL of either 3,5-dimethoxy-4-hydroxycinnamic acid (sinapinic acid) or alpha-cyano-4-hydroxycinnamic acid (4-HCCA) in 1:2 acetonitrile/0.1%TFA (aqueous) (v/v/)] on the sample target. The sample/matrix solution was then allowed to air dry at room temperature prior to analysis.

EXAMPLE 4

Preparation of Samples for Bioassay

Concentrations of HG-1 and Aga-IIIA in samples used in vitro assays were determined by amino acid analyses. Typically, final fractions contained purified peptides at a final concentration of about 15–30 μM. Fractions were stored at –80° C. prior to dilution 100-fold or more into the various assay buffers. When higher concentrations of peptide were assayed, methanol was removed from the samples by placing aliquots of the HPLC fractions (c. 100 μL) in a vacuum centrifuge for 10–15 min.

EXAMPLE 5

Measurement of Calcium Influx in Cells and Nerve Preparations

INDO-1 Assay of Internal Calcium Concentrations in Cells

Cells were grown and maintained in culture as described under Materials and Methods, above. Cells were detached by incubation with 0.5 mM EDTA and loaded with 5 μM Indo-1 acetoxymethyl ester (Molecular Probes, Eugene, Oreg.) in 1% BSA-containing assay buffer (10 mM HEPES pH 7.4 in Hanks balanced salt solution without bicarbonate or phenol red) for 60 minutes at 30° C. Loaded cells were washed twice and resuspended (10$^7$ cells/mL) in assay buffer containing 0.5% BSA and stored on ice until use (<3 hours). Varying concentrations of test compounds or vehicle controls were added to 6 mL of 0.5%. BSA in assay buffer containing c. 3x10$^6$ loaded cells. In addition, 5 μM nitrendipine was also added to IMR-32 cells to block L-type calcium channels, and 30–45 μM valinomycin was added to 192C cells to lower resting membrane potential and to allow rapid depolarization to added extracellular potassium. Samples were incubated for 10 minutes at 30° C. and then aliquoted into three disposable cuvettes. Fluorescence measurements were made in triplicate at 30° C. with a Photon Technology International Model. RF-F3004 spectrofluorometer with excitation at 350 nm and dual emission monochromoters set at 400 and 490 nm. Basal emission signals were acquired for 20 seconds, followed by the addition of 180 μL of a stimulation solution (1 M potassium chloride and 68 mM calcium chloride) to 1.86 mL of incubation mixture in the stirred cuvettes with a computer controlled pump. The emission signals were acquired for an additional 30–50 seconds after depolarization.

Basal and peak emission ratios (400 nm/490 nm) were converted to intracellular calcium concentrations as described for INDO-1 by Grynkiewicz et al. (1985) (i.e., according to the formula: $[Ca++]i=Kd*((R-Rmin)/(Rmax-R))*Sf$, where R is the measured 400 nm/490 nm ratio and the remainder of the terms are constants which describe the spectral properties of INDO-1 and its interaction with free calcium). The values for Rmin, Rmax, and Sf were determined in a 2-point calibration as described in Premack et al. 1995.

For 192C and IMR-32, cells, the calcium concentrations were calculated at the peak of the rise in internal calcium (approx. 10 seconds after potassium addition), while values for the GH-3 cells were either determined at the peak response in the presence of 5 uM nitrendipine (T-currents), or at 40 seconds after potassium addition without added dihydropyridine (combined L- and T-currents). Typical increases in internal calcium were from a baseline of 100–150 nM to stimulated values of close to 1 μM. Concentration effect curves were calculated from the proportion of the rise in internal calcium with added agents, to that observed without test compounds. These data were fit to a four parameter logistic function using the least squares method to determine IC$_{50}$ values.

Independent experiments with calcium antagonists specific for L-type currents (nitrendipine), N-type currents (SNX-111=synthetic omega-conopeptide MVIIA), as well as with less selective calcium antagonists (SNX-230= synthetic MVIIC, and omega-Aga-IIIA and felodipine) were used to verify the pharmacological specificity of the different assay signals.

EXAMPLE 6

Electrophysiological Measurements

A. Whole Cell Patch Clamp of Stably Transfected Cells

Currents were measured by the patch clamp method in the whole cell configuration (Hamill et al. 1981). Electrode resistance ranged from 2–6MΩ. Recordings were made with either an Axopatch 1C or Axopatch 200A amplifier (Axon Instruments, Foster City, Calif.) interfaced to PCLMP6 software (Axon Instruments) for data acquisition and analysis.

Calcium currents were recorded utilizing an external bath solution consisting of (in mM): 100 tetraethylammonium chloride, 52 choline chloride, 15 sodium chloride, 2 calcium chloride, 0.8 magnesium chloride, 10 HEPES, and 7 glucose; adjusted to pH 7.4 with hydrochloric acid and 325 mOsM. Cytochrome c, at 0.1 mg/mL, was added as a carrier to peptide containing solutions. The internal pipette solution consisted of (in mM): 140 cesium methanesulphonate 5 EGTA, 10 HEPES, and 4 magnesium adenosine triphosphate; adjusted to pH 7.2 with cesium hydroxide and 310 mOsM. Peptide effects were assayed on currents elicited by changing, the voltage from a holding potential of –90 mV to 0 mV, as a step pulse of 30 msec. duration every 15 sec. Data were sampled at 5 KHz and filtered at 1 KHz. Leak and capacitance currents were subtracted after measuring currents elicited by 22 mV hyperpolarizing pulses ("P/4" protocol).

In general, HG-1 results are reported as the effect on the peak of the current amplitude obtained without the use of the series resistance compensation circuitry. Additional experiments (see results), which were performed with 80% series resistance compensation showed that HG-1 did not affect the time course of the decay of the current: values for inhibition were, within error, the same with or without the series resistance compensation, as well as with peptide effects measured at different times after the voltage step. For concentration-effect studies, peptide solutions were administered by bath exchange through flow through perfusion. Exchange of the perfusion solution was verified by perfusion of solutions with varying external potassium concentrations and assay of effects on membrane potential.

B. Electrophysiology of Class E Channels in Neurohypophysial Terminals

Male rats were sedated with carbon dioxide, then decapitated by guillotine. The neurohypophysis was ten excised and homogenized in a solution containing 270 mM sucrose, 10 mM HEPES buffer, 0.01 mM posassium-EDTA, pH 7. The isolated neurohypophysial nerve terminals could be identified using an inverted microscope or by immunoblotting following patch-clamping recordings. The terminals were then perfused with Normal Locke's saline (140 mM NaCl, 5 mM KCl, 5 mM $NaCO_3$; 2.2 mM $CaCl_2$, 1 mM $MgCl_2$, 10 mM glucose, 10 mM HEPES, 0.1% bovine serum albumin, pH 7.2) Before recording, the terminals (generally 5–8 μm in diameter) were perfused with 5 mM $Ba^{2+}$-LS containing: 145 mM NaCl, 5 mM $BaCl_2$, 1 mM $MgCl_2$, 10 mM HEPES, 15 mM glucose, 0.02% (w/v) bovine serum albumin (BSA) and 1 μM tetrodotoxin (TTX), pH 7.3. To obtain perforated "whole-terminal" patch recordings (Rae, et al. 1991; Hamil, et al. 1981), freshly made amphotericin B (240 μg/ml) was applied in a pipette solution that contained 135 mm cesium glutamate, 10 mM HEPES, 5 mM glucose, 2 mM $CaC_2$, 1 mM $MgCl_2$ and 20 mM triethylamine (TEA), pH 7.3.

Only perforated terminals with access resistances of 3–5 megaOhms (mΩ) were used for recordings to avoid "run-down." The $Ba_{2+}$ current ($I_{Ba}$) which was activated by depolarizing from –80 to +10 mV and demonstrated both transient and long-lasting components, could be maintained for more than one hour without any run-down under these conditions. $I_{Ba}$ was filtered at 3 kHz and sampled at 10 kHz. pCLAMP (Axon Instruments) was used for acquisition and analysis of data.

EXAMPLE 7

Measurement of Sodium and Potassium Currents in IMR-32 Cells

Sodium and potassium currents in IMR-32 cells were measured using the whole cell patch technique described in Example 6, as previously described (Newcomb et al. 1995), but with the following modifications: The external bath consisted of (in mM): 140 sodium chloride, 5 potassium chloride, 10 HEPES, 2 calcium chloride, 1 magnesium chloride, and 12 glucose, adjusted to pH 7.4 with sodium hydroxide and 305 mOsM. The internal pipette solution consisted of (in mM): 15 sodium chloride, 125 potassium methanesulphonate, 10 HEPES, 11 EGTA, 1 calcium chloride, 2 magnesium chloride and 59 glucose, adjusted to pH 7.4 with potassium hydroxide and 295 mOsM. For peptide application, cells were placed in a flow through chamber (0.5–1 mL/min). HG-1 was applied in saline with 0.1 mg/mL cytochrome c through a small tube placed directly adjacent to the cell.

EXAMPLE 8

Measurement of Currents Through Class A Calcium Channels in Xenopus Oocytes

The cRNA for the alpha-1 subunit described in Mori et al. (1991) was expressed in Xenopus oocytes by standard methods (Goldin, 1992). For expression, cRNA for the alpha-1 subunit was co-injected with cRNA for the rabbit alpha2 and delta (Ellis et al. 1988) and human beta (Williams et al. 1992) subunits in equimolar ratios. Approximately 50 nL was injected per oocyte, with a total cRNA concentration of 0.8 μg/μL.

Currents were recorded, by two-electrode voltage clamp using a solution of 4 mM barium chloride, 38 mM potassium chloride, 36 mM tetraethylammonium chloride, 5 mM 4-aminopyridine, 0.4 mM niflumic acid, 5 mM HEPES (pH 7.5), and 0.1 mg/mL bovine serum albumin. Data were sampled at 5 kHz and filtered at 1 kHz utilizing a OC-725B voltage-clamp amplifier. (Warner Instruments) interfaced to PCLAMP software (Axon Instruments, Foster City, Calif.) for acquisition and analysis. Leak and capacitance currents were subtracted on-line using a P/4 protocol. Voltage pulses to 0 mV from a holding potential of –80 mV were used to elicit currents every 10 s.

EXAMPLE 9

Measurement of Currents Through Potassium Channels in Xenopus Oocytes

The cRNAs from the potassium channel alpha subunit cDNA's described in Tempel et al. (1988) (MKv1.1) and Ramaswami et al. (1990) (hKv1.2, hKv1.4) were injected into oocytes at the following concentrations: mKv1.1, 0.2 μg/μL; hKv1.2, 0.3 ng/μL; and hKv1.4, 0.02 μg/μL.

The external, solution used to record potassium currents was 115 mM sodium chloride, 2.5 mM potassium chloride, 1.8 mM calcium chloride, 10 mM HEPES pH 7.2, 0.1 mg/ml bovine serum albumin. All other procedures were the same as with calcium channels, described in Example 8, except that the test pulses were to +50 mV from a holding potential of –70 mV every 5 sec.

EXAMPLE 10

Isolation of Coding Sequence for HG-2 by Polymerase Chain Reaction

Sequence specific degenerate, primers were synthesized, according to standard methods, based on the N-terminal 6 amino acid sequence of HG-1 shown in FIG. 2A, and using the codon preference from *D. melanogaster*. The gene specific nucleotide: S thus represented by SEQ ID NO: 50. A 3' primer was obtained, using the results of preliminary PCR experiments using the 5' primers.

Unless otherwise indicated, all buffers and reagents described in this Example are as described and/or provided in the 3' RACE System for Rapid Amplification of cDNA Ends kit available from Gibco-BRL (Catalog No. 18373-019).

A. Isolation of Total RNA from *Hysterocrates gigas*

Venom sacs obtained from 3 *Hysterocrates gigas* spiders were homogenized in 8 ml of TRIzol™ solution, then incubated at room temperature for 5 minutes before transferring 1 ml aliquots to Eppendorf tubes. To each one milliliter sample was added 0.2 ml of chloroform. The sample was then shaken rigorously for 15 seconds and incubated for 2–3 minutes prior to centrifuging at 10–12,000×g for 15 min at 4° C. The resulting aqueous phase was transferred to a fresh tube, 2-propanol was added per ml of Trizol according to the ratio provided by the manufacturer (BRL). The mixture was incubated at room temperature for 10 minutes and centrifuged at no more than 12000×g for 10 minutes. The supernatant was removed, and the RNA pellet was resuspended in 75% ethanol (adding at least 1 ml of 75% ethanol per 1 ml of TRIzol solution). The sample was mixed on a Vortex mixer, then centrifuged at no moire than 7500×g for 5 minutes at 4° C. The RNA was then air dried, then was dissolved into 100 µl of DEPC-treated water.

B. Purification of Poly-A mRNA From Total RNA (OLIGOTEX Spin Column Protocol From Qiagen)

The amount of total RNA in the RNA sample was determined by conventional means. When the amount was under 250 µg, the total RNA was dissolved in 250 µl DEPC water. 250 µl of 2×binding buffer and 15 µl OLIGOTEX suspension preheated at 37° C. was then added to the RNA. The tube was mixed by gently flicking at the bottom of the tube, then incubated for 3 min at 65° C. to disrupt secondary structure. The tube was then further incubated for 10 min at room temperature followed by centrifugation for 2. min at maximum speed (approx. 12,000×g). The supernatant was then aspirated, and the pellet was resuspended in 400 µl of Wash buffer. The resulting suspension was added to the top of a Qiagen OLIGOTEX Spin Column. The column was centrifuged for 30 sec at maximum speed, and the flow-through fraction was discarded. The spin column was transferred to a new RNase-free tube and the loading and centrifuging steps repeated. The column was then eluted twice with 100 µl of preheated (70° C.) elution buffer, according to manufacturers specifications.

C. First Strand cDNA Synthesis From Poly-A mRNA

The protocol used is the standard protocol provided in the 3' RACE Kit Gibco-BRL. Up to 50 ng of poly(A)-selected RNA from Part B, above, was combined with DEPC-treated water to a final volume of 11 µl in a 0.5 ml microcentrifuge tube. To the tube was added 1 µl of the 10 µM Adaptor Primer solution. (3' RACE Kit). The tube was mixed, and the reaction was collected by brief centrifugation. The mixture was then heated to 70° C. for 10 min, followed by and chilling on ice for at least 1 min. The tube contents were collected by brief centrifugation and the following components were added:

| | |
|---|---|
| 10 × PCR buffer | 2 ul |
| 25 mM MgCl2 | 2 ul |
| 10 mM dNTP mix | 1 ul |
| 0.1M DTT | 2 ul |

The tube was mixed gently and the reaction was collected by brief centrifugation. The mixture was then equilibrated to 42° C. for 2 to 5 min. One µl of SuperScript II RT (reverse transcriptase) was then added, followed by incubation at 42° C. for 50 m. The reaction was terminated by incubating at 70° C. for 15 min. and chilling on ice. The reaction was collected by brief centrifugation, and 1 ul of RNase H was added to the tube which was then mixed and incubated for 20 min.

D. 3' RACE PCR

The following were added to a 0.5-ml microcentrifuge tube:

| | |
|---|---|
| 10 × PCR buffer (GIBCO kit) | 5 ul |
| 25 mM MgCl$_2$ | 3 ul |
| Distilled water | 36.5 ul |
| 10 mM dNTP mix | 1 ul |
| GSP1* 10 uM | 1 ul |

-continued

| | |
|---|---|
| UAP # 10 uM | 1 ul |
| Taq DNA polymerase (5 units/ul) | 0.5 ul |

Two µl of the cDNA synthesis reaction was added to the tube, followed by gentle mixing. 75 µl of mineral oil was layered over the reaction mixture, which was then collected by brief centrifugation. The reaction mixture was then incubated at 94° C. for 3 min. 35 cycles of PCR were then performed using the following protocol:

Denature 94° C. for 45 s

Anneal 55° C. for 45 s.

Extend 72° C. for 1 min 30 s

The mixture was incubated for an additional 10 min at 72° C., then maintained at 4° C. Ten µl of the amplification products were analyzed by agarose gel electrophoresis and the remainder was stored at −20° C. until use.

E. 5' RACE GlassMAX Isolation Spin Cartridge Purification of cDNA

For each sample to purified, 100 µl of sterilized, distilled water was equilibrated to 65° C., and the binding solution was equilibrated at room temperature. 120 ul of binding solution (6M NaI) was added to the first strand reaction (4.5 volumes of binding solution per volume of DNA solution). The cDNA/NaI solution was transferred to a Glass MAX spin cartridge and was centrifuged at maximum speed for 20 s. The cartridge insert was removed from the tube and the flowthrough was transferred to a microcentrifuge tube. The cartridge insert was returned to the tube and 0.4 ml of cold 1×wash buffer was added to the spin cartridge. The cartridge was then centrifuged at maximum speed for 20 s and the flowthrough was discarded. This wash step was repeated two additional times, and the cartridge was washed two times with 400 µl of cold, 70% ethanol as described above. After removing the final 70% ethanol wash from the tube, the tube was centrifuged at maximum speed for 1 min. The spin cartridge insert was transferred into a fresh sample recovery tube, and 50 µl of sterilized, distilled, water (preheated to 65° C.) was added to the spin cartridge, followed by centrifugation at maximum speed for 20 s to elute the cDNA.

F. TdT Tailing of cDNA

5×Tailing buffer contains the following components:

| | |
|---|---|
| DEPC-treated water | 55 ul |
| 10× reaction buffer | 25 ul |
| 25 mM MgCl2 | 20 ul |

5×buffer has the following final composition:

50 mM Tris-HCl (pH 8.4)

125 mM Kcl 5 mM MgCl2

The following components were added to a 0.5 ml microcentrifuge tube:

| | |
|---|---|
| DEPC-Treated water | 6.5 ul |
| 5× tailing buffer | 5.0 ul |
| 2 mM dCTP | 2.5 ul |
| cDNA sample | 10 ul |

The tube was incubated for 1 to 2 min at 94° C., then was chilled 1 min on ice. The contents of the tube were collected by brief centrifugation and placed on ice. 1 µL TdT was added, followed by gentle mixing, and incubation for 10 min at 37° C. The final composition of the reaction was as follows:

10 mM Tris-HCl (pH 8.4)
25 mM KCl
1.0 mM MgCl2
200 uM dCTP
0.4 units/µl TdT

The TdT mixture was heat inactivated for 10 min at 65° C. to 70° C.

G. PCR Amplification of dC-Tailed cDNA

The following components were added to a fresh 0.5 ml microcentrifuge tube on ice:

29 µl Sterilized, distilled water
4µl 10×reaction buffer
3µl 25 mM MgCl2
1 µl 10 mM DNTP
1µl nested GSP2 (10 µM)
1 µl anchor primer (10 µM)
1 µl dC-tailed cDNA

[GSP1 (SEQ ID NO: 46) and GSP2 (SEQ ID NO: 47) are both degenerate primers designed according to the amino acid sequence of HG1.]

Both UAP and Anchor primer are universal primers provided in the GIBCO-BRL 3' RACE kit described above.

The contents of the tube were mixed, then overlaid with 75 µl mineral oil. The tube was centrifuged briefly to collect the reaction components in the bottom of the tube, then incubated at 94° C. for 5 min and maintained at 80° C. Taq DNA polymerase was diluted to 0.4 units/ul in 1×reaction buffer. Five µl of diluted enzyme was then added to each reaction. The mixture was then subjected to 35 cycles of PCR amplification using the same protocol as described above for 3' RACE. 10 µl of the amplified sample was analyzed by agarose gel electrophoresis, ethidium bromide staining and the appropriate molecular size standards.

H. Cloning of the PCR Product Into pAMP1 Vector (GIBCO-BRL).

The following components were added to a 0.5 ml microcentrifuge tube on ice:

2 µl PCR product (10–50 ng)
2 µl PAMP1 vector DNA (25 ng/ul)
15 µl 1×annealing buffer
1 µl Uracil DNA Glycosylase (1 U/ul)

The components were mixed and incubated at 37° C. for 30 min. After incubation, the reaction tube was placed on ice. After annealing, a portion of the annealing reaction mix (1–5 µl) was used for transformation.

I. Transformation

100 µl of DH5α cells (competent bacterial cells; GIBCO-BRL) were placed in a tube on ice. To the cells was added 1 µl of annealing product, followed by mixing and incubation on ice for 30. min. The mixture was then subjected to heat shock at 42° C. for 45 sec, followed by incubation on ice for 2 min. SOB+ media (0.9 ml) was then added to the tube, which was then shaken at 37° C. for 1 hour. The tube was then centrifuged at 4° C. at no more than 4000 rpm for 5 min. 0.9 ml of the supernatant was then removed and the rest of the cells were plated on LB plate+Carbenicillin+IPTG+X-gal (as substrate for beta-galactosidase). The plates were then incubated at 37° C. overnight.

J. Preparation of Miniscale DNA

Miniscale DNA was prepared to confirm the success of cloning and sequence the positive clones. White colonies were picked from the plate. Individual colonies were incubated in a 37° C. shaker overnight in different tubes containing 5 ml of LB media with Carbenicillin. The DNA was then prepared according to standard methods and were sequenced (e.g., Maniatis et al., 1982).

EXAMPLE 11

Anticonvulsant Activity: DBA/2 Mouse Seizure Model

DBA/2 mice (18–21 days old; approx. 7–10 g) were obtained from Jackson Laboratories, Bar Harbor, Me., and were housed for a minimum of three days to acclimate them to laboratory conditions. On the day of the test, mice were injected i.c.v. into the lateral ventricle with vehicle or test compound (total volume: 5 µl) according to standard methods (Jackson) 30 minutes prior to exposure to sound stimulus. After injection, the mice were individually housed in observation chambers and were observed over the following 30 min. for evidence of shaking behavior (persistent whole body shakes) or any other abnormal behaviors. The animals were exposed to a high intensity sound stimulus (100–110 dB sinusoidal tone at 14 Hz for 30 s). Mice were observed for the presence of clonic and tonic seizures with full hindlimb extension during the 30 s exposure to the sound.

EXAMPLE 12

Synthesis of HG-1 (SNX-482)

Instrumentation: SNX-482 was synthesized on an a Model 433A automated peptide synthesizer (Applied Biosystems Inc., Foster City, Calif.). Analytical HPLC analyses were performed on Model 2350/2360 (ISCO, Lincoln, Nebr.) and Model 1050 (Hewlett Packard, Palo Alto, Calif.) systems. The preparative HPLC system consisted of two Model SD-1 pump (200 mL maximum flow rate pump head), an HPXL pump (25 mL maximum flow rate pump head), an SD-200 pump (50 mL maximum flow rate pump head) and a model D II UV detector (Rainin, Emeryville, Calif.). Amino acid analysis was carried out on a Model 3100 post column ninhydrin derivatization system (Pickering, Mountain View, Calif.) connected with a Model 1050 solvent delivery system (Hewlett Packard, Palo Alto, Calif.). Electrospray ionization mass spectrometry analysis was performed on a VG Biotech BIO-Q instrument with quadrupole analyzer.

Synthesis, Purification and Characterization of the Peptide: For loading the first amino acid to the resin 5 g dry 2-chlorotrityl chloride resin (Novabiochem, San Diego, Calif.) with 1–1.6 mmol/g loading capacity (200–400 mesh) was washed 2× with dry dichloromethane (DCM) and was suspended in 20 mL DCM. A solution of Fmoc-Asp(OtBU)-OH (0.6 mmol 246 mg) in 10 mL dry DCM containing a few drops of dry dimethylformamide (DMF), and 1.3 mL (7.5 mmol) distilled diisopropyl ethylamine (DIPEA) was added to the resin suspension with vigorous shaking. After 45 min, the resin was filtered off, and was treated 3 times for 10 min with DCM/MeOH/DIPEA (17/2/1 v/v). The resin was then washed 3 times with DCM, 2 times with DMF/DIPEA (19/1 v/v), 2 times with DCM/DIPEA (19/1 v/v), 2 times with DMF, 5 times with DCM and 3 times with ethanol (EtOH). Finally the resin was dried in vacuum desiccator over $P_2O_5$.

For each peptide synthesis, 0.8 g of the Fmoc-Asp(OtBu)-2-chlorotrityl chloride resin was used. The side chain of the Fmoc amino acids were protected with the following groups: Asp(OtBu), Lys(Boc), Cys(Trt), Arg(Pmc) or Arg(Pbf), Tyr (tBu), Ser(tBu), Asn(Trt), His(Trt) or His(Boc), Trp(Boc) or unprotected. The activation was carried out using 1 equiv of HBTU and HOBt, and 2 equiv of DIPEA in DMF/NMP mixture. The coupling time was 20 min. The coupling and sterically hindered deprotection was monitored by comparing the conductivity of the piperidine/NMP mixture after each deprotection step. When two consecutive conductivity values were within 15% of each other, the deprotection was stopped. When more then 3 deprotection steps were necessary for an amino acid, the coupling time for the next amino acid was doubled.

The peptide was cleaved from the resin with a mixture of TFA/thioanisole/water/1,2-ethanedithiol (87.5/5/5/2.5 v/v) for 90 min at room temperature. The resin was filtered off, and the solution was poured into ice cold methyl tert-butyl ether (MTBE). The precipitated crude peptide was separated by centrifugation and was washed 3× with MTBE. The crude linear peptide was analyzed on the analytical HPLC system, using solvent A: 0.1% TFA/water and solvennt B: 0.09% TFA/acetonitrile, with a linear gradient of 1% B/min starting at 5%. Vydac (The Separations Group, Hesperia, Calif.) C18, 300 Å pore size, 5 uM particle size, 4.6×250 mm column was used, with a flow rate of 1 mL/min.

Oxidation/folding of the linear peptide was achieved in the following buffer solution: $K_2HPO_4$ (50 mM) prepared with degassed water (pH 8) containing glutathione oxidized (2 mM) glutathione reduced (4 mM). 100 mg crude-peptide was dissolved in 15 mL DMSO, and was added to 50 mL of the above buffer solution while cooling with ice. The pH was adjusted to 9.5 and the mixture was stirred at 4° C. until the oxidation was complete.

The progress of the oxidation was followed by analytical HPLC using solvent A: 20 mM triethyl ammonium phosphate (pH 7) and solvent B: acetonitrile, with a linear gradient of 1% B/min starting at 10%: B. Phenomenex (Torrance, Calif.). A C18 column (300 Å pore size, 5 uM particle size, 4.6×250 mm) was used, with a flow rate of 1 mL/min. Upon completion of the folding, the reaction mixture was diluted with 150 mL ice cold water, the pH was adjusted to 8 and the insoluble material was filtered off.

Preparative purification of the peptide was achieved using the preparative HPLC system with the following eluting solvents: A: 20 mM ammonium acetate (pH 6.8) in water and solvent B: acetonitrile. The gradient was 0.5% solvent B/min starting at 5% B. For the first HPLC purification, the diluted and filtered oxidation mixture was delivered onto a Septech, annular expansion (Wakefield, R.I.) 50×250 mm column, packed with Vydac (The Separations Group, Hesperia, Calif.) C18, 300 Å pore size, 15–20 uM particle size packing material. The flow rate for the gradient separation was 100 mL/min. Fractions containing the peptide were collected and lyophilized. The second purification of the peptide was done on a Vydac C8 pH stable 300 Å pore size, 10 uM particle size, 21×250 mm column, with a flow rate of 15 mL/min. Fractions containing the pure peptide were collected and lyphilized.

The amino acid composition of the purified peptide was determined by hydrolyzing the peptide with 6 N HCl in vacuo, and analyzing the hydrolyzate on a Pickering Model 3100 amino acid analyzer. The disulfide bond arrangement of the synthetic peptide was determined according to the method described by Chung (Chung at al. Int. J. Pept. Prot. Res, 1995, 46, 320–350). Electrospray mass spectroscopy analysis was carried out by injecting 50 microliters of sample aliquot into the instrument source. Elution was carried out using a mixture of 50% acetonitrile/water containing 0.1% TFA, at a flow rate of 10 µl/min. myoglobin was used to calibrate the instrument.

While the invention has been described with reference to specific methods and embodiments, it will be appreciated that various modifications and changes may be made without departing from the invention.

It is claimed:

1. An isolated polynucleotide, comprising a sequence of nucleotides that encodes a peptide selected from the peptides having the sequences defined by SEQ ID NO: 1, SEQ ID NO: 2, SEQ ID NO: 3, SEQ ID NO: 4, SEQ ID NO: 6, SEQ ID NO: 7, SEQ ID NO: 8, SEQ ID NO: 9, SEQ ID NO: 11, SEQ ID NO: 12, SEQ ID NO: 13, SEQ ID NO: 14, and SEQ ID NO: 15.

2. An isolated polynucleotide selected from the polynucleotides having sequences defined by SEQ ID NO: 23 to SEQ ID NO: 43.

3. An isolated polynucleotide comprising a sequence of nucleotides that encodes a peptide having the sequence G V D K $X_1$ G C R Y M F G G C $X_2$ $X_3$ $X_4$ D D C C P $X_5$ L G C $X_6$ $X_7$ $X_8$ $X_9$ S $X_{10}$ Y C A W $X_{11}$ $X_{12}$ T $X_{13}$ $X_{14}$ $X_{15}$ (SEQ ID NO: 54) or CRYMFGGC$X_2$$X_3$$X_4$DDCCP$X_5$LGC$X_6$$X_7$$X_8$$X_9$S$X_{10}$YCAW$X_{11}$$X_{12}$T$X_{13}$$X_{14}$$X_{15}$(SEQ ID NO: 55), where $X_1$ is A or P; $X_2$ is S or E, $X_3$ is V or K, $X_4$ is D or N, $X_5$ is R or K, $X_6$ is H or K, $X_7$ is S or D, $X_8$ is I or L, $X_9$ is F or L, $X_{10}$ is Y or deletion, $X_{11}$ is D or E, $X_{12}$ is L or V, $X_{13}$ is F or G, $X_{14}$ is S or E or deletion, and $X_{15}$ is F or D or deletion.

4. An isolated polynucleotide comprising a sequence of nucleotides that encodes a peptide having the sequence G V D K A G C R Y $X_1$ F G G C $X_2$ $X_3$ $X_4$ D D C CPRLGC$X_5$$X_6$$X_7$$X_8$ $X_9$$X_{10}$YCAWD$X_{11}$TFSD (SEQ ID NO: 56), wherein $X_1$ is selected from Class V; $X_2$ is selected from Class II; $X_3$ is selected from Class IV or V; $X_4$ is selected from Class III; $X_5$ is selected from Class III or Class IV or deletion; $X_6$ is selected from Class IV or V, $X_7$ is selected from Class II or IV; $X_8$ is selected from Class II or V; $X_9$ is selected from Class VI; $X_{10}$ is selected from Class II or III; and $X_{11}$ is selected from Class II, V or VI.

5. The isolated polynucleotide of claim 1, selected from the polynucleotides having sequences def